United States Patent [19]
Fukumoto

[11] Patent Number: 4,896,339
[45] Date of Patent: Jan. 23, 1990

[54] MATERIAL TESTING MACHINE

[75] Inventor: Mitoshi Fukumoto, Tokyo, Japan

[73] Assignee: Matsuzawa Seiki Kabushikikaisha, Tokyo, Japan

[21] Appl. No.: 170,396

[22] Filed: Mar. 18, 1988

[30] Foreign Application Priority Data

Mar. 19, 1987 [JP] Japan .................................. 62-65210
Mar. 19, 1987 [JP] Japan .................................. 62-65211
Mar. 19, 1987 [JP] Japan .................................. 62-65212

[51] Int. Cl.$^4$ ............................................. G01N 3/42
[52] U.S. Cl. ......................................... 377/19; 73/81
[58] Field of Search ........................ 73/81, 82; 377/19

[56] References Cited

U.S. PATENT DOCUMENTS

| | | | |
|---|---|---|---|
| 4,094,188 | 6/1978 | Bellouin et al. | 73/81 |
| 4,111,039 | 9/1978 | Yamawaki et al. | 73/82 |
| 4,312,220 | 1/1982 | Borgersen et al. | 73/81 |
| 4,535,623 | 8/1985 | Gilberto | 73/81 |

Primary Examiner—John S. Heyman
Attorney, Agent, or Firm—Sixbey, Friedman, Leedom & Ferguson

[57] ABSTRACT

A material testing machine includes two detecting means of indenter pressing force detecting means provided with a displacement detector or a strain gage type detector and amount of penetration detecting means provided with a displacement detector. When it is detected by a pulse that the output of the detector of the indenter pressing force detecting means has reached a predetermined value, the output of the detector of the amount of penetration detecting means is latched by the pulse and latched output is used as the output of the amount of pentration detecting means. In a further embodiment, the two detectors are provided with a pulse generator and counting means for counting pulses generated therefrom. When it is detected by a pulse that the output of the detector of the indenter pressing force detecting means has reached a predetermined value the counting means of the amount of penetration detecting means is controlled by the pulse and the output of the counting means is used as the output of the amount of penetration detecting means.

6 Claims, 17 Drawing Sheets

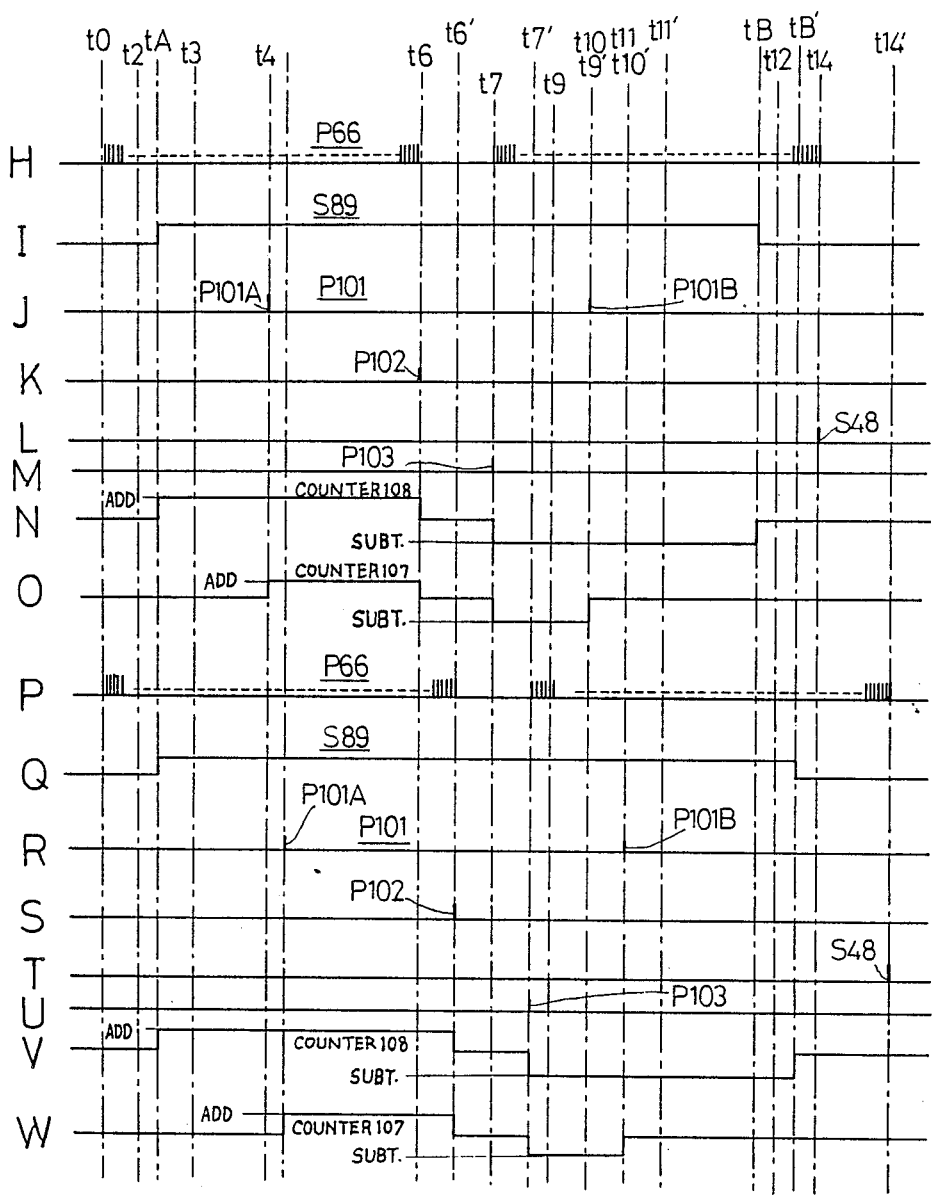
Fig.6 (CON'T)

MATERIAL TESTING MACHINE

BACKGROUND OF THE INVENTION

1. Field of the Invention

The present invention relates to a material testing machine which measures the hardness, tensile strength, yield stress, Young's modulus, creep strength, or the like of a material (which hereinafter referred to simply as the hardness of the material, in the interests of brevity) by pressing an indenter into the surface of the material (hereinafter referred to as a specimen) to make therein an indentation to a predetermined depth. More particularly, the invention pertains to a material testing machine which measures the hardness of a specimen through utilization of either one or both of the amount of penetration of the indenter into the specimen, which corresponds to a first predetermined value of the pressure on the specimen when the indenter is pressed thereinto to the predetermined depth, and the amount of penetration which corresponds to the above-mentioned predetermined first value or a second value of the pressure on the specimen when the indenter is pulled up form the specimen.

2. Description of the Prior Art

As a material testing machine of this type there has been proposed a machine which is equipped with a specimen table for holding a specimen, an indenter for impression into the specimen to make therein an indentation, an indenter pressing member for pressing the indenter into the specimen, indenter pressing force detecting means for detecting the pressure on the specimen form the indenter, and amount of penetration detecting means for detecting the amount of penetration of the indenter into the specimen. In this material testing machine, the amount of penetration detecting means has a displacement detector provided with a stator and a movable element. The stator is fixed to either one of the indenter and the specimen table and the movable element is contacted at its free end with the other one of them.

With such a material testing machine, the pressure on the specimen can be measured using the detected output from the indenter pressing force detecting means and the amount of penetration of the indenter into the specimen can be measured using the detected output from the amount of penetration detecting means not only when the indenter is pressed into the specimen to make therein an indentation but also when the indenter is pulled up away from the specimen. Accordingly, the hardness of the specimen can be measured.

In the conventional material testing machine, however, the indenter pressing force detecting means is complex in structure, imposing severe limitations on the reduction of the whole size on the machine and its manufacturing cost.

Furthermore, according to the prior art machine, since the stator of the displacement detector of the amount of penetration detecting means is fixed to the specimen table or the free end of its movable element is held in contact with the table, the detected output from the displacement detector is affected by the condition of the surface of the specimen table and the condition in which the specimen is held on the table. Moreover, the detected output from the displacement detector of the amount of penetration detecting means contains an error which results from the lowering of the specimen surface relative to the table surface which is caused by the pressure on the specimen from the indenter. Therefore, the amount of penetration of the indenter into the specimen cannot be measured with high accuracy.

Accordingly, the conventional material testing machine cannot accurately measure the hardness of the specimen.

SUMMARY OF THE INVENTION

It is therefore an object of the present invention to provide a novel material testing machine which is free from the above-mentioned defects of the prior art.

The material testing machine of the present invention comprises a specimen table for holding a specimen, an indenter for impression into the specimen to make therein an indentation, an indenter pressing member for pressing the indenter into the specimen, indenter pressing force detecting means for detecting the pressure on the specimen from the indenter, and amount of penetration detecting means for detecting the amount of penetration of the indenter into the specimen, as is the case with the conventional material testing machine.

According to an aspect of the present invention, an indenter pressing force transmitting member is interposed between the indenter pressing member and the indenter, and this transmitting means is made of an elastic material. Further, the indenter pressing force detecting means includes a displacement detector which has a stator fixed to either one of the indenter and the indenter pressing member and a movable element contacted at its free end with the other of them. With such an arrangement, the indenter can be pressed by the indenter pressing member into the specimen through the indenter pressing force transmitting member. In this instance, the transmitting member made of an elastic material is compressed as the indenter is pressed by the indenter pressing member. The amount of compression of the elastic transmitting member corresponds to the pressure on the specimen by the indenter. On the other hand, the displacement detector which serves as indenter pressing force detecting means detects the amount of compression of the elastic member and yields the detected output as an indenter pressing force detected output.

Therefore, as is the case with the conventional material testing machine, the hardness of the specimen can be measured through utilization of the detected output from the indenter pressing force detecting means and the detected output from the amount of penetration detecting means.

However, the material testing machine of the present invention has a simple arrangement in which the indenter pressing force detecting means only involves a displacement detector which has a stator fixed to either one of the indenter and the indenter pressing member and a movable element having its free end held in contact with the other of them and the displacement detector produces the indenter pressing force detected output representing the pressure on the specimen by the indenter.

Accordingly, the material testing machine of the present invention of the present invention can be constructed smaller and at a lower cost than the prior art material testing machine.

According to another aspect of the present invention, the amount of penetration detecting means includes a contactor for contact with the specimen surface and a displacement detector which has a stator and a movable element. The stator is fixed to either one of the indenter and the contactor, and the movable element has its free end held in contact with the other of them. Therefore, the amount of penetration of the indenter into the specimen, which is obtained from the above-said displacement detector, can be obtained regardless of what surface the specimen table has and how the specimen is held on the table. Accordingly, the amount of penetration of the indenter into the specimen, which is measured by the detected output from the amount of penetration detecting means, can be obtained with high accuracy.

According to another aspect of the present invention, the amount of penetration amount detecting means includes (a) pulse generating means which generates a train of pulses in response to a movement of the indenter pressing member for pressing the indenter and (b) counting means which responds to an output from the indenter pressing force detecting means to count the train of pulses until the pressure on the specimen from the indenter changes from a first value to a second value. The counting means yields an amount of penetration detected output which corresponds to a first predetermined value of the pressure on the specimen when the indenter is pressed thereinto to make therein an indentation. Therefore, the amount of penetration detected output can be obtained by the amount of penetration detecting means with a very simple structure. Accordingly, measurement of the hardness of the specimen, which utilizes the above-mentioned amount of penetration of the indenter into the specimen, can be achieved with a simple arrangement.

According to another aspect of the present invention, the amount of penetration detecting means includes (a) pulse generating means which generates a first train of pulses in response to a movement of the indenter pressing member in a first direction for pressing the indenter and generates a second train of pulses in response to a movement of the indenter pressing member in a second direction reverse to the first direction after the movement in the first direction, and (b) counting means which responds to an output from the indenter pressing force detecting means to count, as a first count value, the first train of pulses until the pressure on the specimen from the indenter changes from a first value to a second value and, as a second count value, the second train of pulses until the pressure on the specimen from the indenter changes from the second value to the first value, and which obtains a count value equal to the difference between the first and second count values. The counting means yields an amount of penetration detected output representing the difference between the amount of penetration of the indenter into the specimen which corresponds to a first predetermined value of the pressure on the specimen when the indenter is pressed thereinto to make therein an indentation and the amount of penetration which corresponds to the above-mentioned first value of the pressure on the specimen when the indenter is pulled up from the specimen. Therefore, the amount of penetration detecting means produces, with a simple arrangement, the amount of penetration detected output representing the above-said difference.

Accordingly, measurement of the hardness of the specimen, which utilizes the amount of penetration detected output representing the above-said difference, can be achieved with a simple arrangement.

According to another aspect of the present invention, the amount of penetration detecting means includes (a) pulse generating means which generates a first train of pulse in response to a movement of the indenter pressing member in a first direction for pressing the indenter an a second train of pulses in response to a movement of the indenter pressing member in a second direction reverse to the first direction, (b) a contactor having its free end held in contact with either one of the indenter pressing member or the indenter and the specimen surface, (c) a switch which has first and second contacts provided on the other one of the indenter pressing member or the indenter and the specimen surface and the contactor, respectively, and (d) counting means which responds to an output from the indenter pressing force detecting means to count, as a first count value, the first train of pulses until the pressure on the specimen from the indenter changes from a first value to a second value and, as a second count value, the second train of pulses until the pressure on the specimen from the indenter changes from the second value to the first value, which during the ON state of the switch counts, as a third count value, the first train of pulses and, as a fourth count value, the second train of pulses, and which obtains a count value of the difference between the first and second count values, corrected by the difference between the third an fourth count values. The counting means yields an amount of penetration detected output representing the difference between the amount of penetration of the indenter into the specimen, which corresponds to a first predetermined value of the pressure on the specimen when the indenter is pressed thereinto to make therein an indentation, and the amount of penetration, which corresponds to the above-said first value of the pressure on the specimen when the indenter is pulled up from the specimen. In this case, the detected output thus obtained from the counting means is free from an error which is introduced by lowering of the specimen surface relative to the specimen table owing to the pressing of the specimen by the indenter.

Therefore, the amount of penetration detected output representing the amount of the indenter into the specimen can be obtained, without involving an error, with a simple arrangement.

Accordingly, measurement of the hardness of the specimen, which utilizes the amount of penetration detected output free from an error, can be achieved with a simple arrangement.

DESCRIPTION OF THE PREFERRED EMBODIMENTS

Embodiment 1

Referring first to FIGS. 1A to 1C, 2 and 3A to 3K, a first embodiment of the material testing machine of the present invention will be described in detail.

Figure 1A:
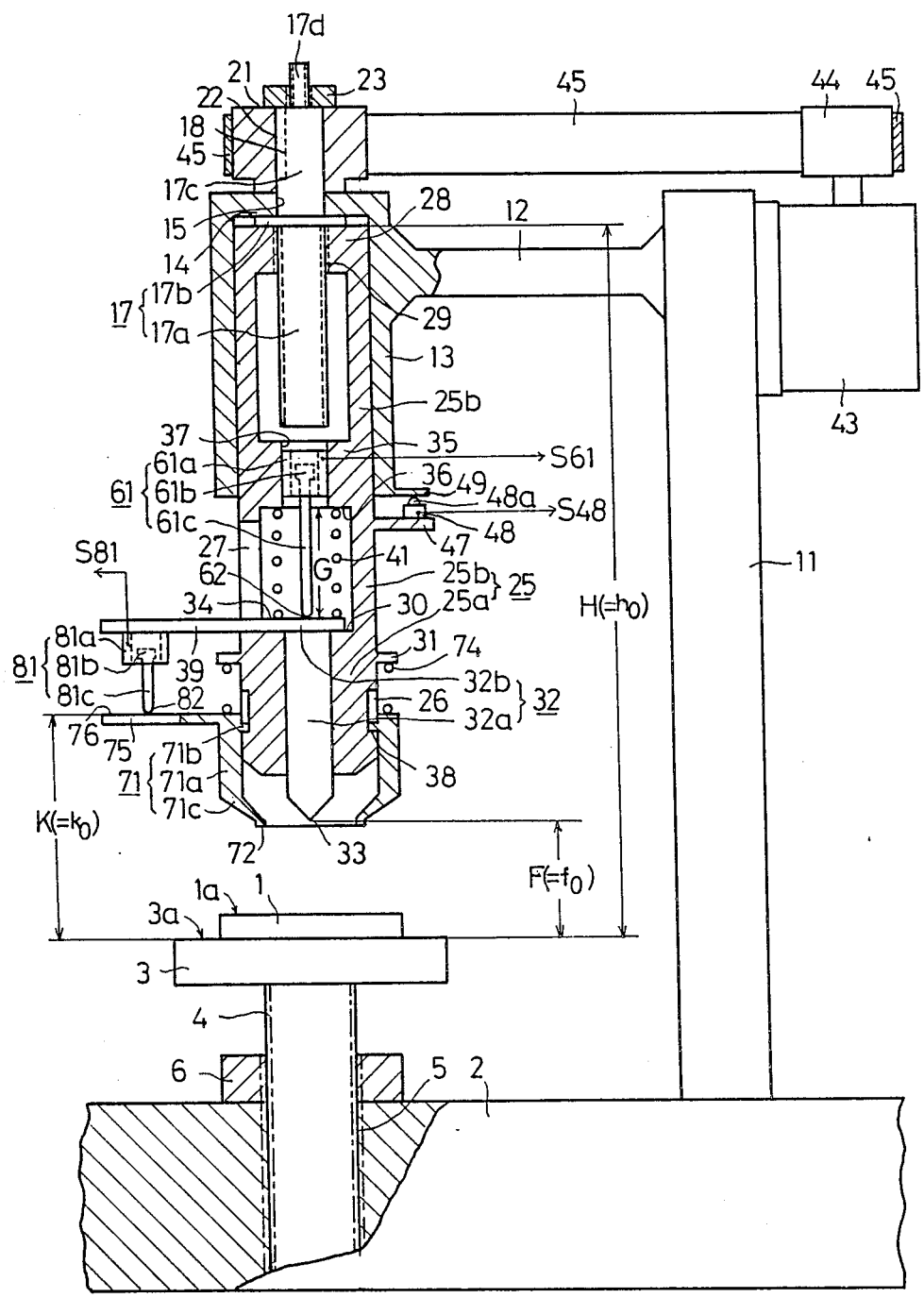
FIGS. 1A to 1C are schematic diagrams, partly in section, illustrating the mechanical system of a first embodiment of the material testing machine of the present invention.
Figure 1B:
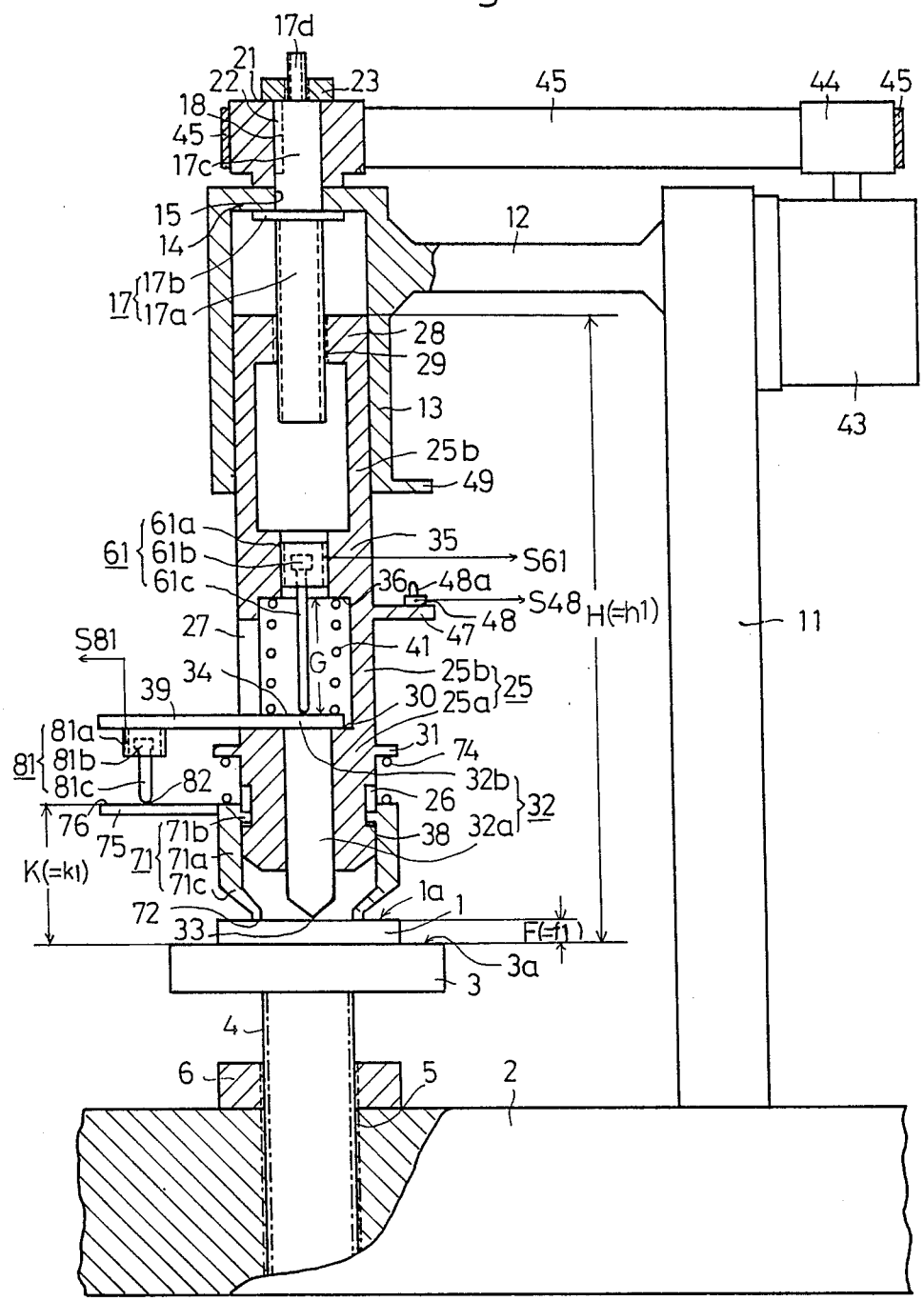
Figure 1C:
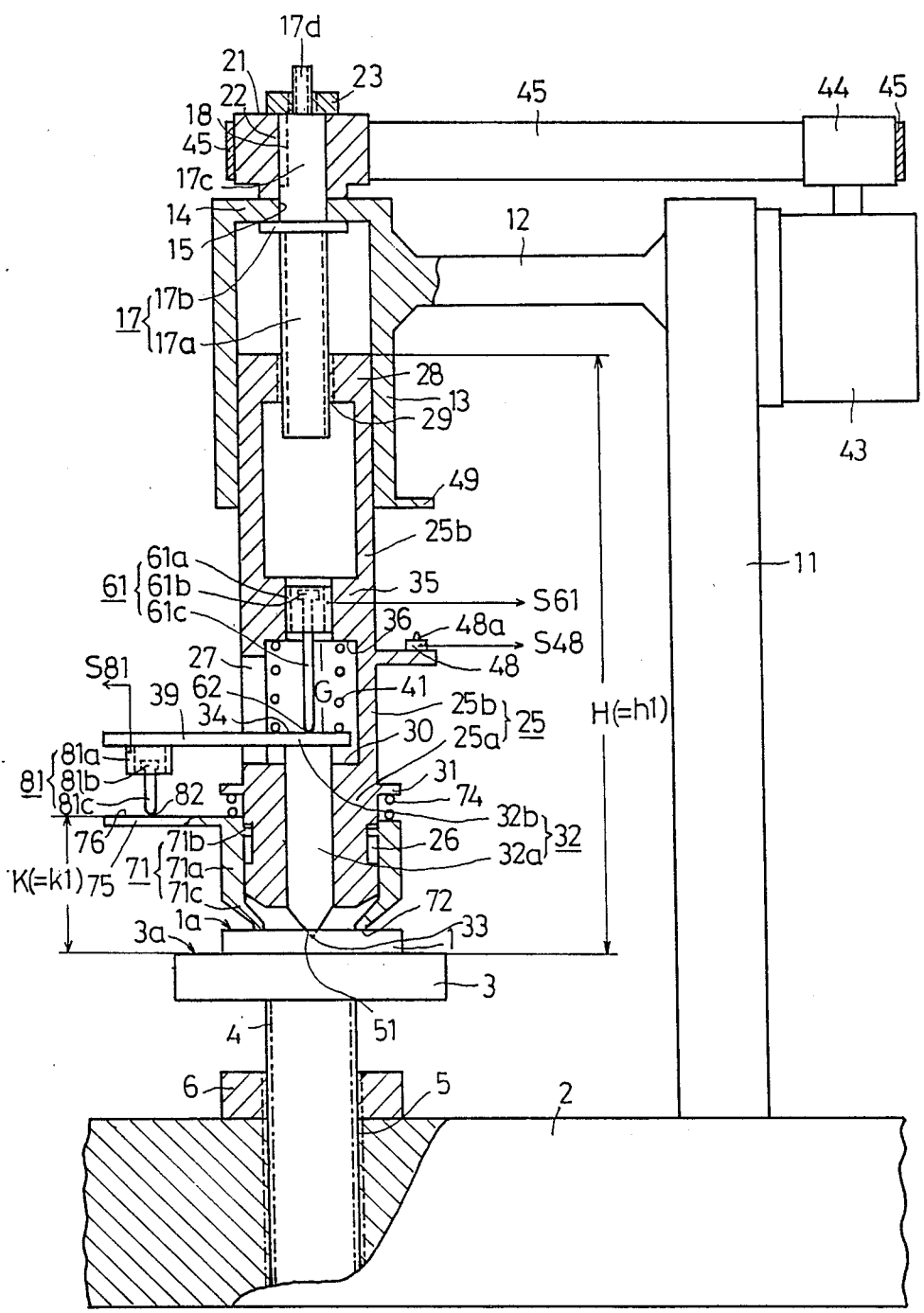

In FIGS. 1A to 1C, reference numeral 3 indicates a specimen table with a flat surface 3a on which is placed a specimen 1 having a flat surface 1a. The specimen table 3 is mounted on the free end of a threaded support shaft 4, as a unitary structure therewith, with the flat surface 3a held in a plane perpendicular to the axis of the threaded support shaft 4. The threaded support shaft 4 is screwed into a vertical screw hole 5 drilled and tapped in a base 2 and is fixed thereto by means of a nut 6. Accordingly, the specimen table 3 is supported in a manner to be movable vertically to the base 2 while holding the surface 3a horizontally.

The base 2 has an upstanding post 11 formed integrally therewith. The post 11 has at its free end a support arm 12 formed as a unitary structure therewith and extending horizontally. The support arm 12 has at its free end a guide sleeve 13 also formed as a unitary structure therewith and extending down at right angles thereto, for guiding an indenter pressing sleeve 25 described later.

The guide sleeve 13 is closed at its upper end with an end plate 14 having a hole 15 made therethrough but is open at its lower end. The guide sleeve 13 is axially aligned with the threaded support shaft 4 and positioned above the specimen table 3.

Reference numeral 17 indicates a driving shaft which is rotatably received in the guide sleeve 3 but does not practically move in its axial direction. The driving shaft 17 has, as a unitary structure, a threaded shaft portion 17a which has an outer diameter smaller than the inner diameter of the guide sleeve 13, a flange 17b which has an outer diameter larger than the inner diameter of the hole 15 of the end plate 14 of the guide sleeve 13, a driving wheel receiving shaft portion 17c which has an outer diameter substantially equal to the inner diameter of the hole 15 and has a key way 18 cut in its outer peripheral surface and extending from its free end face, and a shaft portion 17d which has an outer diameter smaller than the driving wheel receiving shaft portion 17c. The shaft portion 17d and the driving wheel receiving shaft portion 17c are loosely passed through the hole 15 of the end plate 14 from the inside of the guide sleeve 13 until they project out thereof with the flange 17b abutting against the end plate 14. A driving wheel 21 having a key 22 is mounted on the driving wheel receiving shaft portion 17c, with the key 22 fitted in the key way 18 of the latter. A nut 23 is thread-mounted on the shaft portion 17d to affix thereon the driving shaft 21. Thus, the driving shaft 17 is rotatably supported by the guide sleeve 13, with the shaft portion 17d extending coaxially therewith.

Reference numeral 25 identifies an indenter pressing sleeve, which comprises a unitary structure of an indenter guide sleeve portion 25a which has an axially extending circumferential guide groove 26 cut in its outer peripheral surface and having an inner diameter smaller than that of the guide sleeve 13 and a sleeve portion 25b which has an inner diameter larger than that of the indenter guide sleeve portion 25a and an outer diameter substantially equal to the inner diameter of the guide sleeve 13 and has a slit 27 which communicates with the inside of the indenter guide sleeve portion 25a and extends in the axial direction thereof. The indenter pressing sleeve 25 is closed at its upper end with an end plate portion 28 having a tapped hole 29. The driving shaft 17 extends into the sleeve portion 25b, with its threaded shaft portion 17a threadly engaged with the tapped hole 29. The indenter pressing sleeve 28 is slidably received at the sleeve portion 25b in the guide sleeve 13, with the indenter guide sleeve portion 25a projecting out thereof toward the specimen table 3, and hence is telescopically guided up and down by the guide sleeve 13.

In the case, the indenter guide sleeve portion 25a of the indenter pressing sleeve 25 has a flange-like spring bearing portion 31 protrusively provided a little above the guide groove 26.

Reference numeral 32 designates an indenter which is slidably received in the indenter guide sleeve 25. The indenter 32 comprises a shaft portion 32a which has a pointed end 33 and an outer diameter substantially equal to thaw inner diameter of the indenter guide sleeve portion 25a of the indenter pressing sleeve 25 and a disc-shaped pressure receiving portion 32b which is provided on the top of the indenter 32 and has a flat pressure receiving face 34 and an outer diameter larger than the shaft portion 32a. The shaft portion 32a is loosely received in the indenter guide sleeve portion 25a of the indenter pressing sleeve 25 with the pressure receiving portion 32b resting on a stepped portion 30 provided between the indenter guide sleeve portion 25a and the sleeve portion 25b. Thus, the indenter 32 is slidably received in the indenter pressing sleeve 25, with the pointed end 33 projecting out of the indenter guide sleeve portion 25a toward the specimen table 3.

The indenter guide sleeve portion 25b of the indenter pressing sleeve 25 has formed therein and integrally therewith an inwardly protruding pressing portion 35 which has a flat pressing face 36 opposite the pressure receiving face 34 of the indenter 32 in parallel relation thereto. A coiled spring 41 is interposed between the pressure receiving face 34 of the pressure receiving portion 32b of the indenter 32 and the pressing face 36 of the pressing portion 35 of the indenter pressing sleeve 25.

The indenter pressing sleeve portion 25b of the indenter pressing sleeve 25 has a switch mounting piece 47 protrusively provided on the outside thereof. A stop switch 48, which has a movable contact 48a, is mounted on the switch mounting piece 47. On the other hand, a switch receiving piece 49 for contact with the movable contact 48a of the switch is protrusively provided on the guide sleeve 13.

In this instance, the switch mounting piece 47 and the switch receiving piece 49 are provided on the indenter pressing sleeve portion 25b and the guide sleeve 13, respectively, in such a manner that the switch 48 is switched for OFF to ON or vice versa upon contacting the end plate portion 28 with the flange 17b of the driving shaft 17 when the indenter pressing sleeve 25 is brought up from its lowered position where the end plate portion 28 is out of contact with the flange 17b.

A motor 43 having a driving wheel 44 is mounted on the post 11, and the driving wheel 44 and the afore-mentioned driving wheel 21 mounted on the driving shaft 17 are coupled together by means of a belt 45.

With the arrangement described above, when the motor 43 is not being driven and accordingly the driving shaft 17 is not being rotated, the indenter pressing sleeve 25 keeps its end plate portion 28 in abutment against the flange 17b of the driving shaft 17 and the indenter 32 holds its pressure receiving portion 32b on the stepped portion 30 between the indenter guide sleeve portion 25a and the sleeve portion 25b of the indenter pressing sleeve 25, as shown in FIG. 1A. In this state, the pointed end 33 of the indenter 32, projecting out of the open end of the indenter guide sleeve portion 25a of the indenter pressing sleeve 25, is held at a sufficient distance from the specimen table 3 to place the specimen 1 on the specimen table 3.

Driving the motor 43 in its forward direction, the driving shaft 17 is driven in its forward direction via the driving wheel 44, the belt 45 and the driving wheel 21. As the driving shaft 17 is driven, the indenter pressing sleeve 25 holding the indenter 32 is lowered toward the specimen table 3, bringing the pointed end 33 of the indenter 32 into contact with the surface 1a of the specimen 1 held on the specimen table 3, as shown in FIG. 1B.

By further continuing the forward driving of the motor 43 thereafter, the indenter pressing sleeve 25 is further lowered toward the specimen 1, as depicted in FIG. 1C. In this case, the coiled spring 41 is compressed as the sleeve 25 is moved down. Consequently, the indenter pressing sleeve 25 starts to press the indenter 32 through the coiled spring 41 at the same time as the printed end 33 gets into contact the surface 1a of the specimen 1, and then impresses the pointed end 33 of the indenter 32 into the specimen 1, making therein an indentation 51.

After making the indentation 51 in the specimen 1 as described above, the motor 43 is once stopped and then driven in the reverse direction, thus reversing the driving shaft 17. Accordingly, the indenter pressing sleeve 25 is raised together with the indenter 32, by which the pointed end 33 is brought up from the specimen 1 and finally the end plate portion 28 of the indenter pressing sleeve 25 abuts against the flange 17b of the driving shaft 17, when the stop switch 48 s activated. The stop switch 48 yields a stop signal S48 indicating the return of the indenter pressing sleeve 25 to its raised position. The stop signal S48 is applied to control the motor 43 to automatically stop it.

As will be seen from the above, the indenter pressing sleeve 25 constitutes an indenter pressing member for pressing the indenter 32 into the specimen 1. The coiled spring 41 is made of an elastic material and forms an indenter pressing force transmitting means which is interposed between the indenter pressing member and the indenter 32.

A displacement detector 61 for detecting the indenter pressing force is provided in the indenter pressing sleeve 25 which serves as the indenter pressing member. The displacement detector 61 comprises, for example, an air-core electromagnetic transformer 61a formed by windings, an axially movable magnetic piece 61b disposed in its air core and a bar-shaped engaging member 61c extending from the magnetic piece 61b in the axial direction of the sleeve 25 and having an engaging face 62 at its free end. The electromagnetic transformer 61a is fixedly disposed in an axially extending hole 37 defined by the inner wall of the indenter pressing portion 35 of the indenter pressing sleeve 25. The engaging face 62 of the engaging member 61c is held in contact with the pressure receiving face 34 of the pressure receiving portion 32b of the indenter 32.

The electromagnetic transformer 61a of the displacement detector 61 forms a stator of the detector 61 and the magnetic piece 61b and the engaging member 61c form a movable element of the detector 61.

In the case where the displacement detector 61 of the above-mentioned construction is employed, the magnetic piece 61b stays at its reference position in the air-core of the electromagnetic transformer 61a when the pressure receiving portion 32b of the indenter 32 rests on the stepped portion 30 between the sleeve portions 25a and 25b of the indenter pressing sleeve 25, that is, when the pointed end 33 of the indenter 32 is held apart from the surface 1a of the specimen 1, as shown in FIG. 1A. As the indenter pressing sleeve 25 falls and lowers the pointed end 33 of the indenter 32 to the surface 1a of the specimen 1 and then presses thereinto the pointed end 33 while compressing the coiled spring 41, the magnetic piece 61b in the air core of the electromagnetic transformer 61a moves up from the reference position, i.e. in the direction opposite from the indenter 32, as depicted in FIG. 1C. At this time the coiled spring 41 made of an elastic material and serving as an indenter pressing force transmitting means is compressed as referred to above. Accordingly, an output representing the amount of compression of the coiled spring 41 acting as the indenter pressing force transmitting means can be obtained from the electromagnetic transformer 61a serving as the stator of the displacement detector 61 for detecting the indenter pressing force. The amount of compression of the coiled spring 41 corresponds to the pressure on the specimen 1 applied by the indenter 32. Therefore, an indenter pressing force detected output S61, which represents the pressure on the specimen 1, can be obtained from the displacement detector 61.

As will be seen from the above, the displacement detector 61 constitutes an indenter pressing force detecting means for detecting the pressure on the specimen 1 held on the specimen table 3.

A contactor 71 is provided on the indenter pressing sleeve 25. The contactor 71 comprises a sleeve portion 71a which has an inner diameter nearly equal to the outer diameter of the indenter guide sleeve portion 25a of the indenter pressing sleeve 25, an annular engaging portion 71b which extends radially from the interior surface of the sleeve portion 71a near the top thereof and which has a width substantially equal to the depth of the guide groove 26 of the indenter guide sleeve portion 25a and a thickness sufficiently smaller than the length of the guide groove 26, and a conical contacting portion 71c which extends down from the lower end of the sleeve portion 71a inwardly thereof and forms at its free end a contact edge 72 defining an opening of an inner diameter larger than the outer diameter of the shaft portion 32a of the indenter 32. The contactor 71 is mounted on the indenter guide sleeve portion 25a of the indenter pressing sleeve 25, with the engaging portion 71b disposed in the guide groove 26 of the indenter guide sleeve portion 25a.

In this instance, a coiled spring 74 which is sufficiently softer than the above-mentioned coiled spring 41 is interposed between the sleeve portion 71a of the contactor 71 and the annular spring bearing portion 31 protrusively provided on the indenter guide sleeve portion 25a of the indenter pressing sleeve 25. When the pointed end 33 of the indenter 32 is not in contact with the specimen 1 as shown in FIG. 1A, the coiled spring 74 urges the engaging portion 71b of the contactor 71 against the lower end 38 of the guide groove 26 of the indenter guide sleeve portion 25a, holding the contact edge 72 of the contacting portion 71c in a plane slightly below the position where the pointed end 33 of the indenter 32 lies when the pressing portion 32b of the indenter 32 rests on the stepped portion 30 between the indenter guide sleeve portion 25a and the sleeve portion 25b of the indenter pressing sleeve 25.

Furthermore, a displacement detector 81 for detecting the amount of penetration of the indenter 32 into the specimen 1, which is identical in construction with the afore-mentioned displacement detector 61 for detecting the indenter pressing force, is provided separately of the latter.

The displacement detector 81 comprises, for instance, an air-core electromagnetic transformer 81a formed by winding, an axially movable magnetic piece 81b disposed in its air core and a bar-shaped engaging member 81c extending from the magnetic piece 81b in the axial direction of the transformer 81a and having an engaging face 82 at its free end, as is the case with the displacement detector 61. The electromagnetic transformer 81a is fixedly mounted on the underside of a support piece 39 extending from the pressure receiving portion 32b of the indenter 32 radially thereof and projecting out of the slit 27 of the indenter guide sleeve portion 25b of the indenter pressing sleeve 25. The engaging face 82 of the engaging member 81c is held in contact with the top face 76 of a receiving piece 75 extending from the sleeve portion 71a of the contactor 71 radially thereof.

The electromagnetic transformer 81a of the displacement detector 81 for detecting the amount of penetration of the indenter 32 into the specimen 1 constitutes a stator of the detector 81, whereas the a magnetic piece 81b and the engaging member 81c form a movable element of the detector 81.

As the indenter pressing sleeve 25 moves down from its uppermost position where the pointed end 33 of the indenter 32 is held out of contact with the specimen surface 1a of the specimen 1 as shown in FIG. 1A, that is, as the indenter pressing sleeve 25 brings the pointed end 33 of the indenter 32 down into contact with the specimen surface 1a and then presses thereinto the pointed end 33 while compressing the coiled spring 41, the contactor 71 also moves down toward the specimen 1, finally bringing the contact edge 72 into contact with the specimen 1. In this case, the contact edge 72 of the contacting portion 71c makes contact with the specimen surface 1a a little earlier than does the pointed end 33 of the indenter 32, after which even if the pointed end 33 is pressed into the specimen 1 as shown in FIG. 1C after being lowered to its surface 1a as shown in FIG. 1B, the contactor 71 will not be further lowered because the coiled spring 74 for urging it down is soft. Accordingly, the contact edge 72 of the contacting portion 71c, after being contacted with the specimen 1, is also pressed against it through the coiled spring 74, but since the force of the coiled spring 74 is weak, the contact edge 72 is not strongly pushed on the specimen surface 1a, and hence is held at substantially the same position as it is not urged against the specimen surface 1a.

When the contact edge 72 of the contactor 71 stays away from the specimen surface 1a, the magnetic piece 81b of the displacement detector 81 in the air core of the electromagnetic transformer 81a lies at such an initial position as shown in FIG. 1A. When the contact edge 72 of the contactor 71 and the pointed end 33 of the indenter 32 contact the specimen surface 1a, the magnetic piece 81b assumes its reference position after moving up relative to the electromagnetic transformer 81a from its initial position, as shown in FIG. 1B. After the contact edge 72 has once contacted the specimen surface 1a the contactor 71 does not practically move even when the pointed end 33 of the indenter 32 is contacted with the specimen surface 1a and then impressed into the specimen 1. Accordingly, as the pointed end 33 of the indenter 32 is pressed into the specimen 1 after the contact edge 72 of the contactor 71 is brought into contact with the specimen surface 1a, the magnetic piece 81b of the displacement detector 81 moves up relative to the electromagnetic transformer 81a from the above-said reference position in FIG. 1B to its uppermost position as shown in FIG. 1C.

In this case, the amount of travel of the magnetic piece 81b of the displacement detector 81 in the air-core of the electromagnetic transformer 81a from the position which the magnetic piece 81b will assume when the contact edge 72 of the contactor 71 makes contact with the specimen surface 1a to the position which the magnetic piece 81b will take when the pointed end 33 of the indenter 32 makes contact with the specimen surface 1a, is a known constant value.

It is therefore possible to derive from the electromagnetic transformer 81a of the displacement detector 81 an output representing the amount of travel of the pointed end 33 of the indenter 32 when it is pressed into the specimen 1. This amount of travel corresponds to the amount of penetration of the pointed end 33 of the indenter 32 into the specimen 1. Accordingly, the displacement detector 81 yields an output S81 indicating the amount of penetration of the indenter 32 into the specimen 1.

As will be seen from the above, the contactor 71 and the displacement detector 81 make up a means for detecting the amount of penetration of the indenter 32 into the specimen 1.

Figure 2:
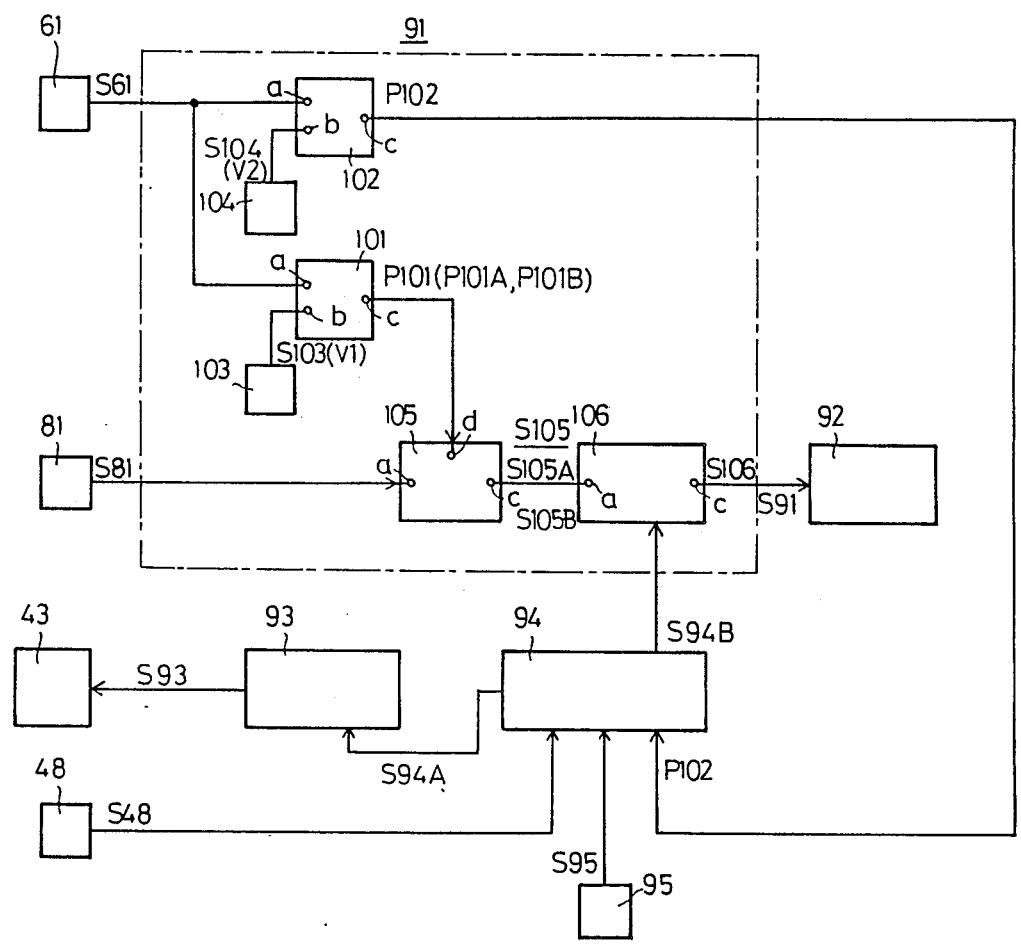
FIGS. 2 is a block diagram illustrating the electrical system of the first embodiment.

FIG. 2 illustrates in block form an electrical system of this embodiment, which includes a processor 91 for processing the indenter pressing force detected output S61 from the displacement detector 61 and the amount of penetration detected output S81 from the displacement detector 81, a display 92 for displaying the processed output S91 from the processor 91, a motor drive circuit 93 for driving the motor 43, a control circuit 94 for controlling the processor 91 and the motor drive circuit 93, and a start switch 95.

The processor 91 is provided with, for example, first and second comparators 101 and 102, a latch circuit 105, and an arithmetic circuit 106.

The first comparator 101 receives at one input terminal a the indenter pressing force detected output S61 from the displacement detector 61 and at the other input terminal b a pressing force set output S103 from a first pressing force setting circuit 103. The output S103 represents, by a first value V1, the pressure on the specimen 1 applied by the indenter 32. The first comparator 101 provides a pulse P101 at its output terminal c when the detected output S61 is equal to the value V1 of the set output S103.

The second comparator 102 similarly receives at one input terminal a the indenter pressing force detected output S61 and at the other input terminal b a pressure set output S104 from a second pressing force setting circuit 104. The output S104 represents, by a second value V2, the pressure on the specimen 1 applied by the indenter 32. The second comparator 102 provides a pulse P102 at its output terminal c when the detected output S61 is equal to the value V2 of the set output S104.

The latch circuit 105 receives at its input terminal a the detected output S81 from the indenter penetration amount detecting displacement detector 81 and at its control terminal d the pulse P101 from the output terminal c of the first comparator 101, and provides at its output terminal c an amount of indenter penetration detected output S105 which indicates the detected output S81 at the time point when the pulse P101 is obtained.

The arithmetic circuit 106 has its input terminal a connected to the output terminal c of the latch circuit 105 and is placed under control of a control signal S94B from the control circuit 94. The arithmetic circuit 106 detects the difference between the detected output S105 (hereinafter referred to as a detected output S105A) which is applied thereto from the latch circuit 105 when a first pulse (hereinafter referred to as a pulse P101A) is obtained from the first comparator 101 and the detected output S105 (hereinafter referred to as a detected output S105B) which is yielded from the latch circuit 105 when the next pulse P101 (hereinafter referred to as a pulse P101B) is provided from the first comparator 101. The arithmetic circuit 106 applies via its output terminal c the detected output S106, as the processed output S91 of the processor 91, to the display 92.

The display 92 displays the contents of the processed output S91 from the processor 91.

The control circuit 94 receives a start signal S95 from the start switch 95 which is produced by its activation, the stop signal S48 from the stop switch 48 and the pulse P102 from the second comparator 102 of the processor 91, and controls the motor drive circuit 93 as described below.

Assuming that the start signal S95, the pulse P102 and the stop signal S48 are applied thereto in this order, the control circuit 94 controls the motor drive circuit 93 by a control signal S94A in such a manner as to stop the motor 43 before the generation of the start signal S95, drive the motor 43 in the forward direction from the time of generation of the start signal S95 to the time of generation of the pulse P102 and drive the motor 43 in the reverse direction a certain period of time after the generation of the pulse P102 to the time of generation of the stop signal S48.

As described above, the control circuit 94 controls the arithmetic circuit 106 of the processor 91 by the control signal S94B to obtain therefrom the operated output S106 as the processed output S91 of the processor 91.

Next, a description will be given, with reference to FIGS. 3A to 3K, of the operation of the material testing machine constructed as described above.

Now, let it be assumed that the start switch 95 in FIG. 2 is activated at a time point t0. Then, the start switch 95 yields the start signal S95 at t0, as shown in FIG. 3A, which is applied to the control circuit 94.

The control circuit 94 responds to the start signal S95 to control the motor drive circuit 93 by the control signal S94A so that the motor 43 is driven by the motor drive signal S93 in the forward direction. In consequence, the motor 43 held at a standstill until then starts forward rotation at t0, as shown in FIG. 3B, and at the same time, the indenter pressing sleeve 25 held at a height H equal to a reference value h0 before t0 starts to descend at a constant speed correspondingly, as depicted in FIG. 3C; namely, the height H of the indenter pressing sleeve 25 decreases at a fixed speed after t0. In this instance, the height H of the indenter pressing sleeve 25 represents the height from the surface 3a of the specimen table 3 to the top of the end plate portion 28 of the indenter pressing sleeve 25, for example. The reference value h0 indicates the height H of the indenter pressing sleeve 25 when the end plate portion 28 of the indenter pressing sleeve 25 is held in contact with the flange 17b of the driving shaft 17 as shown in FIG. 1A.

Figure 3:
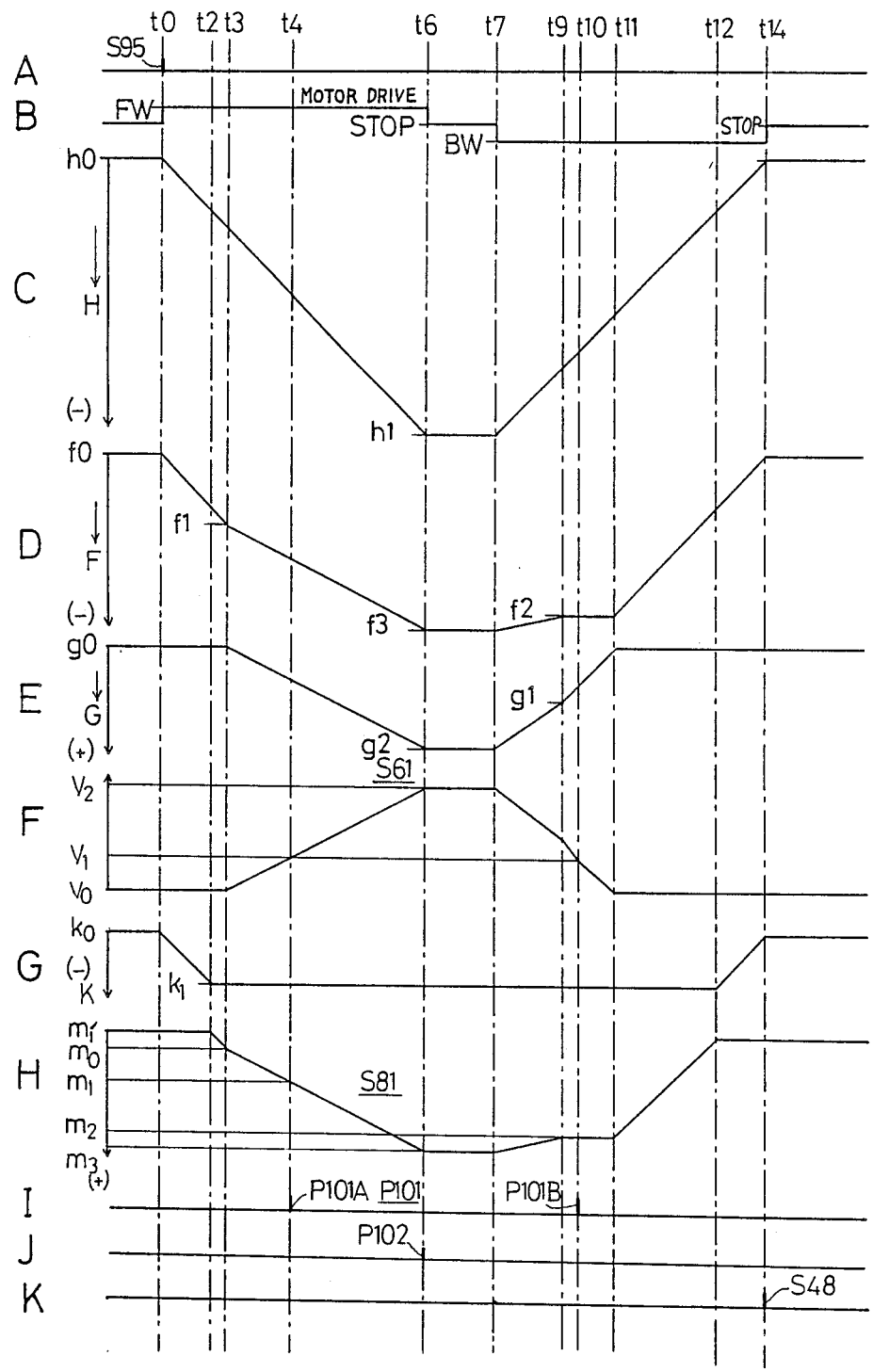
FIGS. 3A to 3K are diagrams explanatory of the operation of the first embodiment.

As the indenter pressing sleeve 25 moves down, the indenter 32 held at a height F equal to a reference value f0 before t0 starts to go down at the same speed as does the indenter pressing sleeve 25, as shown in FIG. 3D. Consequently, the height F of the indenter 32 decreases at the same speed as the height H of the indenter pressing sleeve 25 after t0. The height F of the indenter 32 represents the height from the table surface 3a to the pointed end 33 of the indenter 32, for example. The reference value f0 indicates the height F of the indenter 32 when the height H of the indenter pressing sleeve 25 assumes the reference value h0 and the pressure receiving portion 32b of the indenter 32 rests on the stepped portion 30 of the indenter pressing sleeve 25.

As the indenter 32 goes down, its pointed end 33 also lowers and comes into contact with the specimen surface 1a at a time point t3, as shown in FIG. 1B. At this time, the height F of the indenter 32 assumes a value f1, which represents the thickness of the specimen 1.

The indenter pressing sleeve 25 further goes down after bringing the pointed end 33 of the indenter 32 into contact with the specimen surface 1a at t3. As a result of this, the indenter pressing sleeve 25 pushes, through the coiled spring 41, the indenter 32 towards the specimen 1, impressing thereinto the pointed end 33 after t3. In this instance, since the indenter pressing sleeve 25 further compresses the coiled spring 41 after t3 as well, it continues to descend at the same speed as before, as shown in FIG. 3C, but after this time point the indenter 32 moves down at a lower speed than before, as shown in FIG. 3D.

Since the indenter pressing sleeve 25 and the indenter 32 start to go down at t0, as mentioned above, the amount of compression G of the coiled spring 41 assumes, for example, a zero reference value g0 from the time point t0 to t3 as depicted in FIG. 3E, but thereafter it increases with the lapse of time. The speed at which the amount of compression G of the coiled spring 41 increases corresponds to the difference between the decreasing speed of the height H value of the indenter pressing sleeve 25 shown in FIG. 3C and the decreasing speed of the height F value of the indenter 32 shown in FIG. 3D.

When the amount of compression G of the coiled spring 41 starts to increase at t3, as mentioned above, the pressure receiving face 34 of the pressure receiving portion 32b of the indenter 32 rises relative to the indenter pressing sleeve 25 at the same speed as the amount of compression G of the coiled 41 increases. At the same time, the magnetic piece 61b of the displacement detector 61, which is integral with the engaging member 61c engaging the pressure receiving face 34 of the pressure receiving portion 32b of the indenter 32, is also raised relative to the transformer 61a of the displacement detector 61 from the reference position in the air core of the electromagnetic transformer 61a at the same speed as the amount of compression G of the coiled spring 41 increases.

As a result of this, the indenter pressing force detected output S61 from the electromagnetic transformer 61a of the displacement detector 61 assumes, for example, a zero reference value V0 before t3, but thereafter increases at a speed corresponding to that of the upward movement of the magnetic piece 61b relative to the transformer 61a, i.e. corresponding to the speed of increase in the amount of compression G of the coiled spring 41, as depicted in FIG. 3F.

On the other hand, at the same time a the indenter pressing sleeve 25 and the indenter 32 start to fall at t0 as described above in connection with FIG. 3C and 3D, the contactor 71 held at a height K equal to a reference value k0 also starts to fall at the same speed as the indenter pressing sleeve 25 and the indenter 32, as depicted in FIG. 3G. The height K of the contactor 71 represents the height from the specimen table surface 3a to the top face 76 of the receiving piece 75 of the contactor 71, for example. The reference value k0 indicates the height K of the contactor 71 when the engaging portion 71b of the contactor 71 rests on the lower end face of the guide groove 26 cut in the indenter guide sleeve portion 25a of the indenter pressing sleeve 25.

When the contacting member 71 goes down after t0 and accordingly the value of the height K of the engaging member 71 decreases with the lapse of the time after t0, as described above, the contact edge 72 of the contactor 71 gets into contacts with the specimen surface 1a at t2 before point t3 when the pointed end 33 of the indenter 32 contacts the specimen surface 1a. Although the contact edge 72 of the contactor 71 is in contact with the specimen surface 1a after t2, the indenter pressing sleeve 25 and the indenter 32 further go down as before, as mentioned above with respect to FIG. 3C and 3D. Accordingly, after t2 the indenter pressing sleeve 25 presses through the coiled spring 74 the contactor 71 toward the specimen 1. Since the force of the coiled spring 74 is sufficiently small, however, the contactor 71 is not practically impressed into the specimen 1 and stays at the same height as at the time point t2; namely, the value k1 of the height K at t2 remains unchanged thereafter.

After t2 the contactor 71 stays at the height K equal to the value k1 but the indenter 32 still further goes down, as described above, the magnetic piece 81b of the displacement detector 81, held in contact with the top face 76 of the receiving piece 75 provided in association with the contactor 71, starts to rise relative to the transformer 81a of the displacement detector 81 from a position lower than the reference position in the air core of the electromagnetic transformer 81a, passing through the reference position at the same speed as the indenter 32 lowers.

In consequence, the electromagnetic transformer 81a of the displacement detector 81 yields the detected output S81 which assumes a value m1' larger than, for example, a zero reference value m0 before t2 and thereafter decreases at the same speed as the magnetic piece 81b rises relative to the transformer 81a, as shown in FIG. 3H.

Thus, the value of the detected output S61 from the displacement detector 61 increases with the lapse of time after t3 as shown in FIG. 3F, whereas the value of the detected output S81 from the displacement detector 81 decreases with the lapse of time after t2 as shown in FIG. 3H. Where at a time point t4 the value of the detected output S61 coincides with the value V1 of the pressing force set signal S103 from the pressing force setting circuit 103 in FIG. 2, the comparator 101 yield the pulse P101A as depicted in FIG. 3I which is applied to the latch circuit 105. The latch circuit 105, which is being supplied with the detected output S81 from the displacement detector 81, yields at t4 the detected output S105A corresponding to the value m1 which the detected output S81 assumes at t4. The detected output S105A thus obtained is provided to the arithmetic circuit 106.

In the case where the value of the detected output S61 from the displacement detector 61 coincides with the value V2 of the pressing force set signal S104 from the pressing force setting circuit 104 in FIG. 2 at a time point t6 after t4, the comparator 102 yields the pulse P102 at t6, as shown in FIG. 3J. The pulse P102 is applied to the control circuit 94.

Upon receiving the pulse P102, the control circuit 94 controls the motor drive circuit 93 by the control signal S94A so that the motor 43 stops at t6 and starts to rotate in the reverse direction at a time point t7 a certain period of time thereafter.

Since the motor 43 stands still from t6 to t7 and then starts reverse rotation at t7, as shown in FIG. 3B, the indenter pressing sleeve 25 correspondingly stops the downward movement at t6 and remains at a standstill until t7 as shown in FIG. 3C. Accordingly, the value h1 of the height H of the indenter pressing sleeve 25 at t6 remains unchanged until t7. At t7 the indenter pressing sleeve 25 starts to rise at the same speed as its descending speed during the time interval between t0 and t6.

Furthermore, since the indenter pressing sleeve 25 is at a standstill during the time interval between t6 and t7, the indenter 32 is also at a standstill correspondingly, as shown in FIG. 3D. Accordingly, the value f3 of the height F of the indenter 32 at t6 remains unchanged until t7 and the value g2 of the amount of compression G of the coiled spring 41 similarly remains unchange until t7, as depicted in FIG. 3E.

Yet, since the indenter pressing sleeve 25 climbs after t7, the amount of compression G of the coiled spring 41 gradually diminishes from the above-mentioned value g2 correspondingly.

If the specimen 1 is not substantially elastic, then the indenter 32 will not be subject to force from the specimen 1 and hence will not essentially rise even if the amount of compression G of the coiled spring 41 starts to decrease at t7. However, the specimen 1 is usually elastic, and hence applies upward force to the indenter 32. As the amount of compression G of the coiled spring 41 decreases from t7, the indenter 32 goes up from time t7 to t9 at which it is nc longer subject to the upward force by the specimen 1, as shown in FIG. 3D; namely, the height F of the indenter 32 increases from the value f3 after t7.

Therefore, the amount of compression G of the coiled spring 41 diminishes from time t7 to t9 at a speed lower than that of the upward movement of the indenter pressing sleeve 25.

As described above, during the time interval between t7 and t9 the indenter 32 moves up and the amount of compression G of the coiled spring 41 decreases at a speed lower than that of the upward movement of the indenter pressing sleeve 25. Since the indenter 32 is not subject to the upward force form the specimen 1 after t9, it does not rise although the indenter pressing sleeve 25 further moves up as before. In other words, the height F of the indenter 32 remains at the value f2 after t9, as shown in FIG. 3D. In consequence, after t9 the amount of compression G of the coiled spring 41 decreases from its value g1 at the time point t9, at the same speed as that of the upward movement of the indenter pressing sleeve 25.

Since the amount of compression G of the coiled spring 41 remains unchanged at the value g2 during from time t6 to t7 and decreases at a speed lower than that of the upward movement of the indenter pressing sleeve 25 from time t7 to t9 but at the same speed after t9 as described above, the magnetic piece 61b of the displacement detector 61, disposed in the air-core of the electromagnetic transformer 61a thereof, stays at the same position as at t6 during the time interval between t6 and t7 but, after t7 rises relative to the transformer 81a at the same speed as the amount of compression G of the coiled spring 41 decreases As a result of this, the detected output S61 from the electromagnetic transformer 61a of the displacement detector 61 assumes the value V2 from time t6 to 7 but thereafter decreases at a speed corresponding to the rise of the magnetic piece 61b relative to the transformer 61a, i.e. the decrease in the amount of compression G of the coiled spring 41, as depicted in FIG. 3F.

On the other hand, the height F of the indenter 32 assumes the value f3 during the time interval between t6 and t7, then increases with time from t7 to t9 and thereafter takes the value f2 as described above. Since the height K of the contacting member 71 remains at the value k1 after t9 as well, the magnetic piece 81b of the displacement detector 81 stays at the same position as at t6 during the time interval between t6 and t7, then goes down relative to the transformer 81a at the same speed as the increase in the height F of the indenter 32 during the time interval between t7 and t9 and stays there after t9.

As a result of this, the detected output S81 from the electromagnetic transformer 81 of the displacement detector 81 assumes a value m3 from the time point t6 to t7, then increases at a speed corresponding to that of the downward movement of the magnetic piece 81c relative to the transformer 81a during the time interval between t7 and t9 and thereafter takes a value m2, as shown in FIG. 3H.

That is to say, the value of the detected output S61 from the displacement detector 61 for detecting the indenter pressing force diminishes from V2 after the time point t7, as shown in FIG. 3F, and the value of the detected output S81 from the displacement detector 81 for detecting the amount of impression of the indenter 32 into the specimen 1 increases from m3 during the time interval between t7 and t9 and thereafter at m2, as shown in FIG. 3H. In the case where the value of the detected output S61 coincides with the value V1 of the pressure set output S103 from the pressure setting circuit 103 at a time point before or after t9 which rime point will hereinafter be referred to as a time point t10 after t9), the first comparator 101 yields at t10 the pulse P101B as a pulse next to the pulse P101A, as shown in FIG. 3I, and the pulse P101B is applied to the latch circuit 105.

The latch circuit 105, which is being supplied with the detected output S81 from the displacement detector 81, creates at the time point t10, as an output S105B next to the amount of penetration detected output S105A, the detected output S105B which has the value of the detected output S81 obtained at t10. The detected output S105B is provided to the arithmetic circuit 106.

Since at t4 the arithmetic circuit 106 was supplied with the detected output S105A which had the value of the amount of penetration detected output S81 obtained at t4, the circuit 106 operates the difference between the detected output S105A and the detected output S105B after t10 and provides the operated output S106 as the processed output S91 of the processor 91 to the display 92 for display its contents.

Also after t9 the indenter pressing sleeve 25 continues to rise, but since the indenter 32 does not rise after t9 as mentioned above, the pressure receiving portion 32b of the indenter 32 is received by the stepped portion 30 of the indenter pressing sleeve 25 after t10.

Hence, the amount of compression G of the coiled spring 41 returns to the reference value g0 at a time point t11, and at the same time the indenter 32 ascends together with the indenter pressing sleeve 25.

Since the amount of compression G of the coiled spring 41 thus returns to the reference value g0 at t11, the indenter pressing force detected output S61 from the displacement detector 61 also returns to the reference value V0 at t11.

Moreover, since the indenter 32 further goes up after t11, the engaging member 71b of the contactor 71 is received by the lower end face 38 of the guide groove 26 of the indenter pressing sleeve 25 after t11, so that after a time point t12 the contactor 71 moves up from the position where its contact edge 72 is held in contact with the specimen surface 1a, at the same speed as the indenter 32 rises.

Since the indenter 32 moves up after t11 and the contact member 71 also goes up at the same speed as the indenter after t12, as mentioned above, the magnetic piece 81b of the displacement detector 81 in the air-core of its electromagnetic transformer 81a moves down relative to the transformer 81a at the same speed as that of the upward movement of the indenter 32 during the time interval between t11 and t12 and thereafter stands still.

Therefore, the value of the detected output S81 from the displacement detector 81 increases form m2 with the lapse of time from t11 to t12 at a speed corresponding to that of the fall of the magnetic piece 81b relative to the transformer 81a and returns to m1' at t12.

Where the indenter pressing sleeve 25 moves up together with the indenter 32 after t11 as referred to above and the end plate portion 28 abuts against the flange 17b of the driving shaft 17 at a time point t14, the stop switch 48 is immediately activated and yields the stop signal S48 as depicted in FIG. 3K, and the signal S48 is provided to the control circuit 94.

The control circuit 94 responds to the stop signal S48 to control the motor drive circuit 93, stopping the motor 43 at t14 as shown in FIG. 3B. In consequence, the indenter pressing sleeve 25 returns to the initial state in which its end plate portion 28 is held in contact with the flange 17b of the driving shaft 17. This completes a series of operations of the first embodiment shown in FIG. 1A to 1C and 2.

As will be understood from the above, according to the first embodiment of the present invention, the output S91 which is ultimately provided from the processor 91 corresponds to the difference between the amount of penetration of the indenter 32 into the specimen 1 at t4 when the pressure on the latter has been increased up to the value V1 from the reference value V0 for impressing the indenter 32 into the specimen 1 to make therein the indentation 51 (which amount of penetration will herebelow be identified as m1 which is the same as the value m1 of the amount of penetration detected output S81, for convenience of description) and the amount of penetration of the indenter 32 into the specimen 1 at t10 when the pressure on the latter has been reduced down to the value V1 from the largest value V2 after making the indentation 51 (which amount of penetration will hereinbelow be identified as m2 which is the same as the value m2 of the indenter penetration amount detected output S81, for convenience of description). That is, the above-mentioned output S91 indicates the difference between the above two amounts of penetration, (m2−m1). This difference (m2−m1) is displayed on the display 92.

The above difference (m2−m1) corresponds to the hardness or tensile strength of the specimen 1, though not described in detail.

Accordingly, the material testing machine of the present invention illustrated in FIG. 1A to 1C and 2 permits measurement of the hardness and tensile strength of the specimen 1 through utilization of the amounts of penetration m1 and m2.

The above described material resting machine is advantageous in that the means for detecting the pressure of the indenter 32 on the specimen, which is utilized for obtaining the amounts of penetration m1 and m2, is the simple-structured indenter pressing force detecting displacement detector 61.

Moreover, the testing machine possesses the advantage that the means for detecting the amounts of penetration m1 and m2 of the indenter 32 into the specimen 1 is also a simple-structured amount of penetration detecting displacement detector 81 and that the detected output S81 from the displacement detector 81 is obtained regardless of what surface the specimen table 3 has and how the specimen 1 is held on the specimen table 3. Accordingly, the amounts of penetration m1 and m2 can be obtained with high accuracy.

Embodiment 2

Next, a description will be given of a second embodiment of the material testing machine of the present invention.

This embodiment is identical in construction with the first embodiment except the following point, though not shown and not described in detail.

As described above, according to the first embodiment, in the processor 91 the amount of penetration detected outputs S105A and S105B, which correspond to the values m1 and m2 of the detected outputs S81 (FIG. 3H) yielded by the displacement detector 81 at t4 and t10, respectively, are obtained using the pulses P101A and P101B (FIG. 3I) which are produced when the indenter pressing force detected output S61 (FIG. 3F) from the displacement detector 61 takes the value V1 at both t4 and t10. The operated output S106 corresponding to the difference between the detected outputs S105A and S105B is provided as the processed output S91 to the display 92. On the other hand, according to the second embodiment of the present invention, the abovementioned amount of penetration detected output S105A and the detected output, which corresponds to the value m3 of the detected output S81 yielded by the displacement detector 81 at t6 (which output will hereinbelow be identified as S105C), are obtained using the above-mentioned pulse P101A and the pulse P102 (FIG. 3J) which is produced when detected output S61 assumes the value V2 at t6. The difference between the outputs S105A and S105C is operated and the operated output is applied as the processed output S91 to the display 92. No detailed description is deemed strictly necessary to those skilled in the art and therefore none will be given relating to the construction of the second embodiment in the interests of brevity.

As will be seen from the above, the second embodiment detects the difference between the amount of penetration m1 of the indenter 32 into the specimen 1 when the pressure on the latter has increased up to the value V1 from the reference value V0 for impressing the indenter 32 into the specimen 1 to make therein the indentation 51 and the amount of penetration m3 of the indenter 32 into the specimen 1 when the pressure on the latter has reached the value V2 for making the indentation 51 of a predetermined depth. The difference in the amount of penetration, (m3−m1) is provided to the display 92.

Since this difference (m3−m1) corresponds to the yield stress of the specimen 1, though not described in detail, the second embodiment of the present invention permits measurement of the yield stress of the specimen 1 through utilization of the above-noted amounts of penetration m1 and m3.

Embodiment 3

Next, a third embodiment of the present invention will be described, which is identical in construction with the first embodiment except the following point, though not described in detail.

According to the third embodiment, the amount of penetration detected outputs S105B and S105C which correspond to the values m2 and m3 of the detected output S81 produced by the displacement detector 81 at t10 and t6, respectively, are obtained using the pulses P101B and P102 which are yielded at t10 and t6. The difference between the detected outputs S105B and S105C is calculated and is then provided as the processed output S91 to the display 92.

As will be seen from the above, the processed output S91 thus obtained corresponds to the difference, (m3−m2), between the amount of penetration m3 of the indenter 32 into the specimen 1 detected when the former is impressed into the latter to make therein the indentation 51 to the largest depth as predetermined (i.e. when the value V2 of the pressure on the latter is reached) and the amount of penetration m2 detected when the value V1 of the pressure on the specimen 1 is reached in the upward movement of the indenter 32 after making the indentation 51.

The difference in the amount of penetrations, (m3−m2), thus obtained represents the Young's modulus of the specimen 1, though not described in detail. Accordingly, it is possible, with this embodiment, to measure the Young's modulus of the specimen 1 through utilization of the above-mentioned amounts of penetration m3 and m2.

Embodiment 4

Next, a fourth embodiment of the present invention will be described, which is also identical in construction with the first embodiment except the following point.

According to this embodiment, though neither shown nor described in detail, the amount of penetration detected output S105C, which corresponds to the value m3 of the detected output S81 from the displacement detector 81 at t6, is obtained using the pulse P102 which is yielded at t6 when the value of the indenter pressing force detected output S61 is V2. The detected output S105C thus obtained is provided as the processed output S91 to the display 92. Since the arrangement for the above operation can easily be designed by those skilled in the art, no further description will be given.

As will be seen from the above, the processed output S91 corresponds to the amount of penetration m3 of the indenter 32 into the specimen 1 detected when the former is impressed into the latter to make therein the indentation 51 to the predetermined depth (i.e. when the value of the pressure on the specimen 1 is V2).

The amount of penetration m3 thus detected represents the creep strength of the specimen 1, though not described in detail. Accordingly, this embodiment permits measurement of the creep strength of the specimen 1 through utilization of the above-noted amount of penetration m3.

Embodiment 5

Referring next to FIGS. 4A to 4C and 5, a fifth embodiment of the present invention will be described in detail.

In FIGS. 4A to 4C and 5 the parts corresponding to those in FIGS. 1A to 1C and 2 are identified by the same reference numerals and characters and no detailed description will be given of them.

This embodiment is identical in construction with the first embodiment described previously in connection with FIGS. 1A to 1C and 2, except the omission of the displacement detector 81 for detecting the amount of penetration of the indenter 32 into the specimen 1.

Figure 4A:
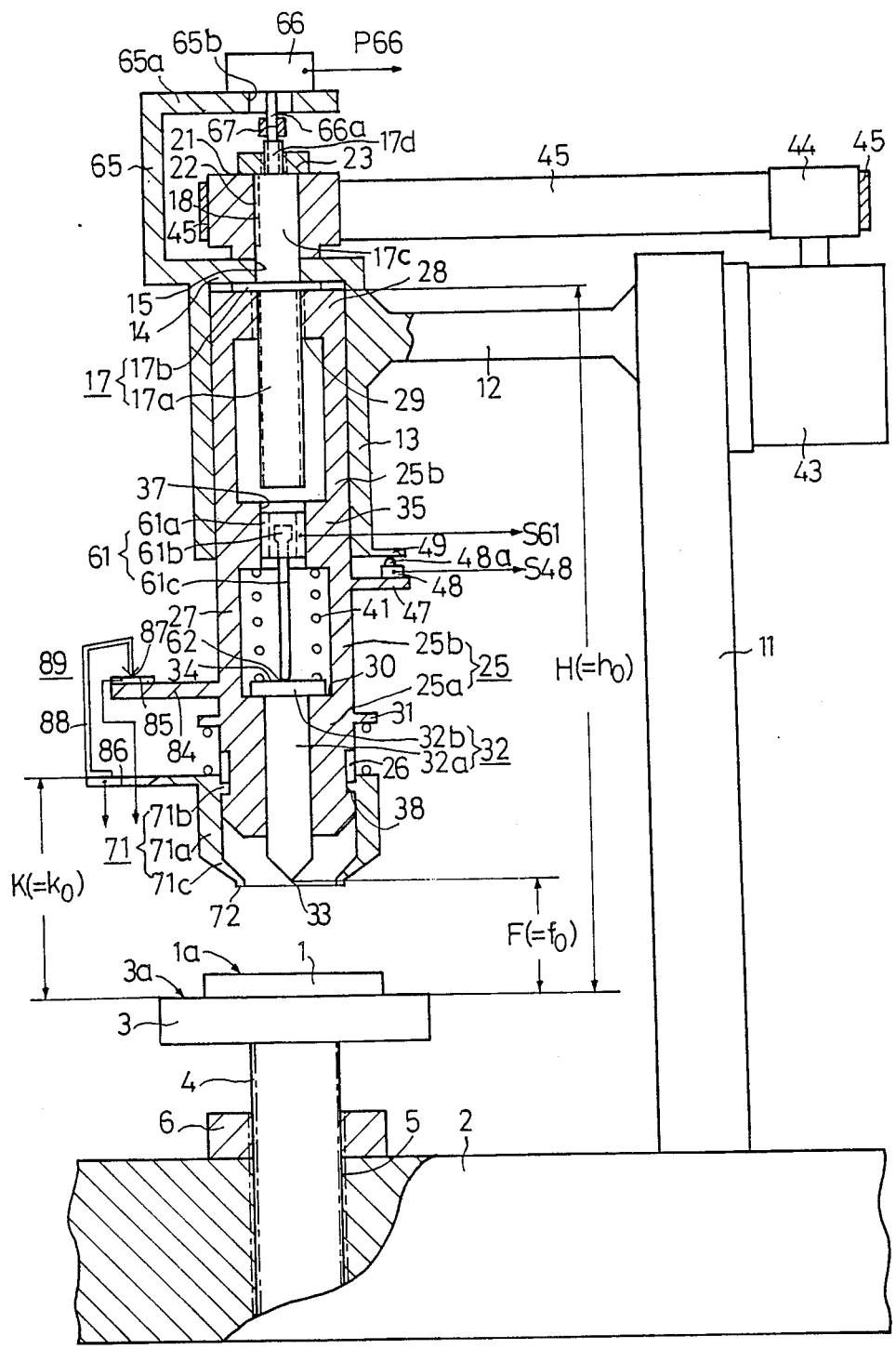
FIGS. 4A to 4C are schematic diagrams, partly in section, illustrating the mechanical system of a fifth embodiment of the material testing machine of the present invention.

As illustrated in FIG. 4A, the guide sleeve 13, which guides up and down the indenter pressing sleeve 25 as described previously, has a fixture 65 which is molded integrally with the end plate portion 14 of the sleeve 13. The fixture 65 has a mounting plate portion 65a opposite in parallel to the free end face of the driving shaft 17 which is rotatably received in the indenter pressing sleeve 25 for moving it up and down. On the mounting plate portion 65a a known rotary pulse generator 66 is mounted with its shaft 66a extending down to the vicinity of the upper free end of the driving shaft 17 through a through hole 65b of the mounting plate portion 65a and coupled to the driving shaft 17 by means of a coupling 67.

The rotary pulse generator 66 generates a train of pulses P66 in response to the rotation of the driving shaft 17 by the motor 43 in both of the forward and reverse directions.

The indenter pressing sleeve 25 descends or ascends depending on whether the driving shaft 17 is driven in the forward or reverse direction. The rotary pulse generator 66 yields the train of pulses P66 of a frequency corresponding to the speed of the upward or downward movement of the sleeve 25.

A support piece 84 is provided which is molded integrally with the indenter pressing sleeve 25, for example near the lower end portion of its sleeve portion 25b and extends therefrom radially. A contact 85 having a flat surface is mounted on the support piece 84. In this case, when the support piece 84 is electrically conductive, the contact 85 is mounted thereon through an insulator (not shown).

Another support piece 86 is provided which is molded integrally with the sleeve portion 71a of the contactor 71 and projects out therefrom radially. On the support piece 86 an elastic piece 88 is mounted which carries at its free end a contact 87 which is held in touch with the contact 85. In this instance, when the contactor 71 and the elastic piece 88 are electrically conductive, the elastic piece 88 is mounted on the support piece 86 through an insulator or the contact 87 is attached to the elastic piece 88 through an insulator.

The contacts 85 and 87 are positioned relative to each other on the support piece 84 and the elastic piece 88, respectively, and the elasticity of the elastic piece 88 is predetermined so that the contact 87 will disengage from the contact 85 when the indenter pressing sleeve 25 lowers from its highest position, where the end plate portion 28 is in contact with the flange 17b of the driving shaft 17 as shown in FIG. 4A, to the position where the contact edge 72 of the contactor 71 gets into contact with the specimen surface 1a (which position will hereinafter be referred to as a first position) or a position (which will hereinafter be referred to as a third position) between the first position and the position where the indenter pressing sleeve 25 presses the indenter 32 into contact with the specimen surface 1a (which position will hereinafter be referred to as a second position).

The contacts 85 and 87 form a switch 89, which serves as amount of penetration detecting means, together with the contacting member 71, as described later.

Figure 4B:
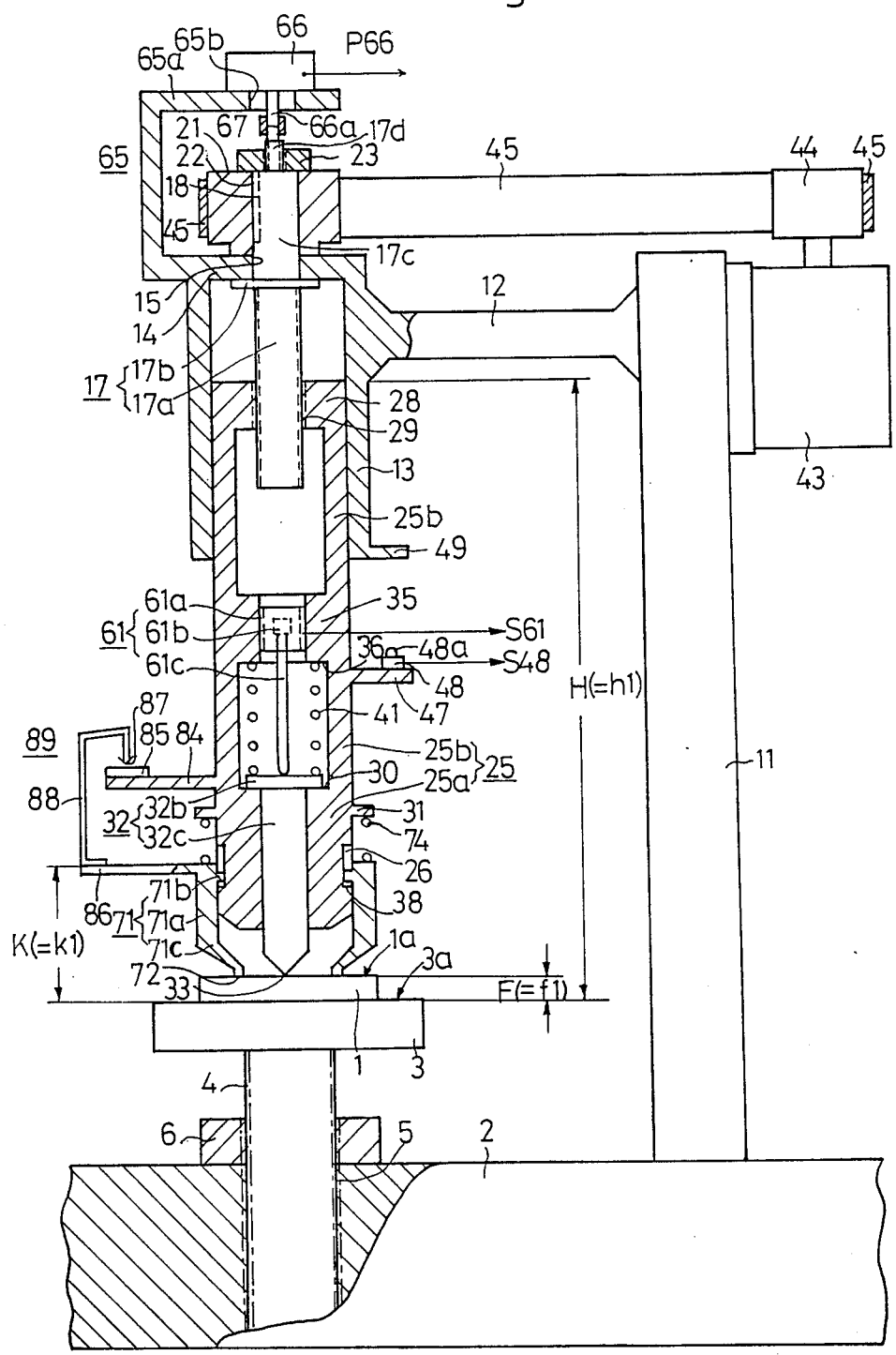
Figure 4C:
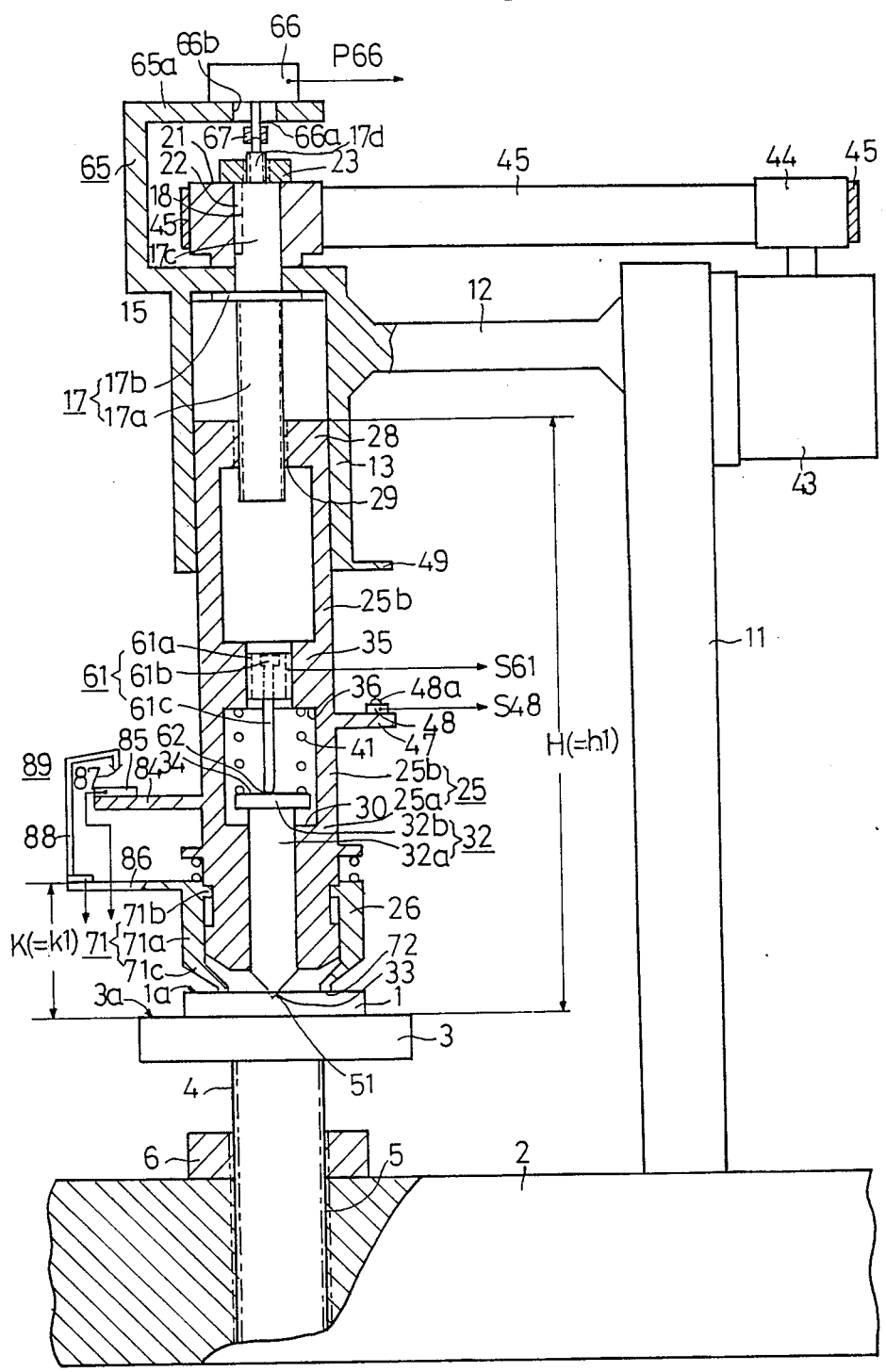

The contact 85 disengages from the contact 87 at or after the time point when the contact edge 72 of the contactor 71 lowers into contact with the specimen surface 1a, and thereafter remains disengaged from the contact 87 until or after the pointed end 33 of the indenter 32 is brought down into contact with the specimen surface 1a, as shown in FIGS. 4B and 4C. In other words, the switch 89 is turned OFF upon contacting of the contact edge 72 with the specimen surface 1a. Accordingly, the switch 89 yields a signal S89 representing its ON-OFF operation.

Figure 5:
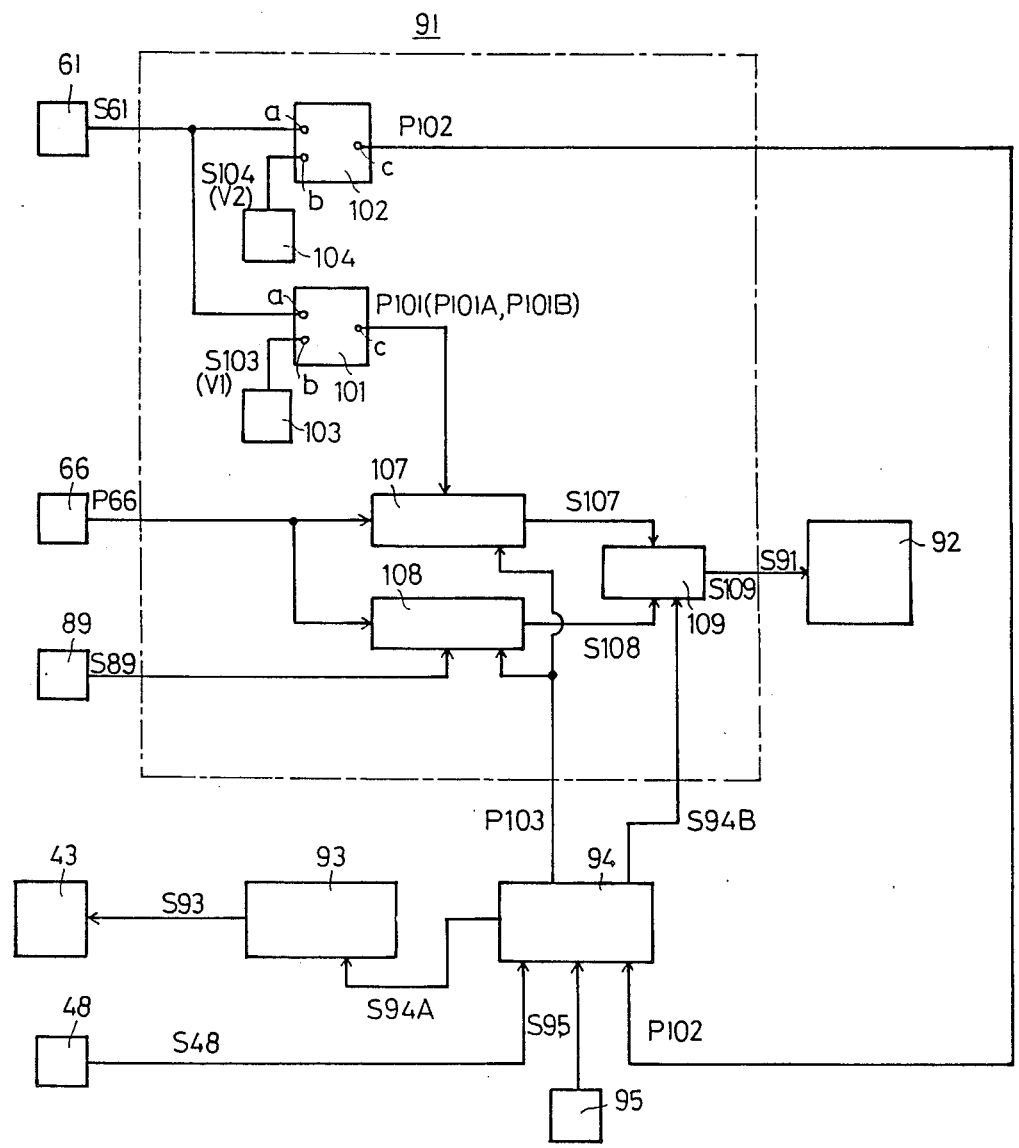
FIGS. 5 is a block diagram illustrating the electrical system of the fifth embodiment.

FIG. 5 illustrates in block form the electrical system of this embodiment, which comprises the processor 91 which is supplied with the indenter pressing force detected output S61 from the indenter pressing force detecting displacement detector 61, the pulse train S66 from the rotary pulse generator 66 and the switch signal S89 from the switch 89, the display 92 for displaying the processed output S91 from the processor 91, the motor drive circuit 93 for driving the motor 43, the control circuit 93, and the start switch 95.

The processor 91 includes, for example, the first and second comparators 101 and 102 such as described previously with respect of FIG. 2, a counter 107 which responds to the first pulse P101A from the comparator 101 to immediately start counting the pulses P66 from the rotary pulse generator 66, a counter 108 which responds to the switch signal S89 from the switch 89 to start counting the pulses P66 upon turning-ON of the switch 89, and an arithmetic circuit 109 which obtains the difference between the count output S107 from the counter 107 and the count output S108 from the counter 108 and provides the operated output S109, as the processed output S91 of the processor 91, to the display 92.

The counter 107 responds to the pulse P101A from the comparator 101 to start additive counting of the pulses P66 from the rotary pulse generator 66 upon reception of the pulse P101A, as described above, while on the other hand the counter 107 starts subtractive counting of the pulses P66 in response to a pulse which is provided from the control circuit 94 in response to the pulse P102 from the comparator 102 but delayed behind it, and continues the subtractive counting until receiving a pulse P103 from the control circuit 94 after the pulse P101A from the comparator 101.

The counter 108 responds to the signal S89 to start additive counting of the pulses P66 upon turning-ON of the switch 89, as described above, while on the other hand it responds to the above-mentioned pulse P103 from the control circuit 94 to start subtractive counting of the pulses P66 upon reception of the pulse P103 and continues the subtractive counting until the switch 89 is turned OFF.

The arithmetic circuit 109 obtains the difference between the count outputs S107 and S108 from the counters 107 and 108 in response to the control signal S94B which is provided from the control circuit 94 after completion of the subtractive counting of the pulses P66.

Next, a description will be given, with reference to FIGS. 6A to 6W, of the operation of the fifth embodiment constructed as described above. FIGS. 6A to 6G correspond to FIGS. 3A to 3G and FIGS. 6J, 6K and 6L correspond to FIGS. 3I, 3J and 3K, respectively.

The fifth embodiment of the present invention depicted in FIGS. 4A to 4C and 5 operates in the same manner as does the first embodiment shown in FIGS. 1A to 1C and 2, except in connection with the rotary pulse generator 66, the switch 89 and the processor 91. Therefore, the following will describe the operation of the fifth embodiment except operations which are not directly associated with the rotary pulse generator 66, the switch 89 and the processor 91.

The start switch 95 in FIG. 5 is turned ON at t0 as in the case of the first embodiment. Upon activation the switch 95 yields the start signal S95, as shown in FIG. 6A, which is applied to the control circuit 94.

As in the first embodiment, the control circuit 94 responds to the start signal S95 to control by the control signal S94A the motor drive circuit 93, applying therefrom the motor drive signal S93 to the motor 43 for driving it in the forward direction. The motor 43 held at a standstill before t0 thus starts forward rotation at t0 as depicted in FIG. 6B. At the same time as the start of forward rotation of the motor 43, the indenter pressing sleeve 25 held at the height H of the reference value h0 before t0 starts to descend at a constant speed as shown in FIG. 6C. Accordingly, the height H of the indenter pressing sleeve 25 decreases at a constant rate after t0.

As the indenter pressing sleeve 25 lowers, the indenter 32 held at the height F of the reference value f0 before t0 also goes down at the same speed as does the indenter pressing sleeve 25, as shown in FIG. 6D. Accordingly, the height F of the indenter 32 also decreases at the same rate as that of the sleeve 25 after t0.

The pointed end 33 of the indenter 32 makes contact with the specimen surface 1a at t3 as depicted in FIG. 6D in the same manner as in the first embodiment.

The indenter pressing sleeve 25 further goes down after contacting the indenter 32 with the specimen surface 1a at t3 as in the first embodiment. Consequently, after t3 the indenter pressing sleeve 25 presses, through the coiled spring 41, the indenter 32 against the specimen 1, impressing the pointed end 33 into the specimen 1 to make therein the indentation 51.

As the indenter pressing sleeve 25 and the indenter 32 descend after t0, the amount of compression G of the coiled spring 41, which assumes the zero reference value g0 during the time interval between t0 to t3, increases after t3, as depicted in FIG. 6E.

With such an increase in the amount of compression G of the coiled spring 41 after t3, the pressure receiving face 34 of the pressure receiving portion 32b of the indenter 32 also rises, after t3, relative to the indenter pressing sleeve 25 at the same speed as the amount of compression G increases. As a result of this, after t3 the magnetic piece 61b of the displacement detector 61, which is unitary with the engaging piece 61c held in contact with the above-mentioned pressure receiving face 34, goes up relative to the electromagnetic transformer 61a from the reference position in the air core of the electromagnetic transformer 61a at the same speed as the amount of compression G of the coiled spring 41 increases.

Accordingly, as in the first embodiment, the displacement detector 61 yields the indenter pressing force detected output S61 which assumes the zero reference value V0 before t3 and thereafter increases at the same rate as the speed of the movement of the magnetic piece 61b relative to the electromagnetic transformer 61a and consequently the rate of increase in the amount of compression G of the coiled spring 41, as shown in FIG. 6F.

On the other hand, as the indenter pressing sleeve 25 and the indenter 32 descend after t0 as described above with regard to FIGS. 6C and 6D, the contactor 71 held at the height K of the reference value k0 also goes down after t0 at the same speed as the indenter pressing sleeve 25 and the indenter 32, as shown in FIG. 6G.

With the downward movement of the contactor 71 after t0, i.e. as its height decreases with time after t0, the contact edge 72 makes contact with the specimen surface 1a at t2 before the pointed end 33 of the indenter 32 is brought down to the specimen surface 1a at t3, as in the first embodiment. The indenter pressing sleeve 25 and the indenter 32 continue their downward movement also after contacting the contact edge 72 of the contacting member 71 with the specimen surface 1a at t2, as referred to above in connection with FIGS. 6C and 6D. After t2 the indenter pressing sleeve 25 urges, through the coiled spring 74, the indenter 32 toward the specimen 1 as in the first embodiment. However, since the force of the coiled spring 74 is sufficiently small, the contactor 71 is not practically impressed into the specimen 1. Hence, the contactor 71 remains at the height of the value k1 after t2.

Since the height of the contactor 71 remains unchanged from the value k1 after t2 and since the height F of the indenter 32 decreases with time after t2 as well, the contact 85 on the support piece 84 extending from the indenter pressing sleeve 25 disengages from the contact 87 provided on the contact member 71 through the support piece 86 and the elastic piece 88 at t2 when the height H of the indenter pressing sleeve 25 takes a value hA or at a time point a little thereafter (which time point will hereinafter be referred to as tA). Accordingly, the switch 89 held in the ON state before tA is turned OFF at tA, yielding the switch signal S89 in the ON state, as depicted in FIG. 6I. The switch signal S89 is applied to the counter 108.

On the other hand, as the indenter pressing sleeve 25 goes down after t0 as described above, the rotary pulse generator 66 yields the pulses P66, as shown in FIG.

6H, which are provided to the counters 107 and 108 of the processor 91.

The counter 108 responds to the switch signal S89 to start additive counting of the pulses P66 at tA, as shown in FIG. 6N.

The value of the indenter pressing force detected output S61 of the displacement detector 61 increases with time after t3, as depicted in FIG. 6F. Where the value of the detected output S61 coincides with the value V1 of the pressure set signal S103 from the pressure setting circuit 103 in FIG. 5 at t4, the comparator 101 yields the pulse P101A as the first pulse of the pulse P101 at t4, as shown in FIG. 6J, which is applied to the counter 107 of the processor 91. The counter 107 responds to the pulse P101A to start additive counting of the pulses P66 at t4, as depicted in FIG. 6O.

Where the value of the detected output S61 from the displacement detector 61 coincides with value V2 of the pressure set signal S104 from the pressure setting circuit 104 at t6, the comparator 102 yields the pulse P102 at t6, as shown in FIG. 6K, which is provided to the control circuit 94.

The control circuit 94 responds to the pulse P102 to apply the control signal S94A to the motor drive circuit 93 to control it so that the motor 43 stops at t6 and after certain elapsed time starts reverse rotation at t7.

Accordingly, the motor 43 stands still during the time interval between t6 and t7 and starts to rotate in the reverse direction at t7 as depicted in FIG. 6B. In consequence, the indenter pressing sleeve 25 stops its downward movement at t6 and remains at a standstill until t7, as shown in FIG. 6C; namely, the value h1 of the height H of the indenter pressing sleeve 25 at t6 remains unchanged until t7. After t7 the indenter pressing sleeve 25 rises at the same speed as that of its downward movement during the time interval between t0 and t6, as in the first embodiment.

Similarly the indenter 32 stands still from t6 to t7 as in the case of the first embodiment and as shown in FIG. 6D, and therefore the value f3 of the height F of the indenter 32 at t6 remains unchanged until t7 and the value g2 of the amount of compression G of the coiled spring 41 at t6 remains unchanged until t7, as shown in FIG. 7E.

However, since the indenter pressing sleeve 25 moves up after t7, the value of the amount of compression G of the coiled spring 41 correspondingly decreases with time from the value g2 after t7.

If the specimen 1 has practically no elastic restoring force, then the indenter 32 will not be subject to upward force from the specimen 1, and hence will not essentially rise even if the amount of compression G of the coiled spring 41 decreases after t7. In general, however, the specimen 1 has elastic restoring force. Therefore the indenter 32 receives upward force from the specimen 1, so that as the amount of contraction G of the coiled spring 41 diminishes after t7, the indenter 32 ascends from t7 to t9 when it is no longer subject to the upward force from the specimen 1, as shown in FIG. 6D. That is, after t7 the height F of the indenter 32 increases from the value f3 at t6.

Accordingly, the amount of contraction G of the coiled spring 41 decreases from t7 to t9 at a rate lower than the speed of the upward movement of the indenter pressing sleeve 25.

As described above, the indenter 32 rises from t7 to t9 and the amount of contraction G of the coiled spring 41 correspondingly decreases at a rate lower than the speed of the upward movement of the indenter pressing sleeve 25. As in the case of the first embodiment, however, the indenter 32 is not subject to the upward force from the specimen 1 after t9, and hence does not ascend regardless of the further upward movement of the indenter pressing sleeve 25 after t9. That is, the value f2 the height F of the indenter 32 at t9 remains unchanged thereafter. As a result of this, after t9 the amount of contraction G of the coiled spring 41 decreases from the value g1 at the same rate as the speed of the rise of the indenter pressing sleeve 25.

Since the amount of compression G of the coiled spring 41 remains at the value g2 from t6 to t7, decreases from t7 to t9 at a rate lower than the speed of the upward movement of the indenter pressing sleeve 25 and thereafter decreases at the same rate as that of the sleeve 25, as described above, the magnetic piece 61b of the displacement detector 61, which is formed as a unitary structure with the engaging piece 61c held in contact with the pressure receiving face 34 of the pressure receiving portion 32b of the indenter 32, stays at the same position in the air of core of the electromagnetic transformer 61a as at t6 until t7 but thereafter moves up relative to the electromagnetic transformer 61a at the same speed as that of the decrease in the amount of compression G of the coiled spring 41.

In consequence, the electromagnetic transformer 61a of the displacement detector 61 yields the detected output S61 which takes the value V2 from t6 to t7 and thereafter decreases with time at the rate corresponding to that of the upward movement of the magnetic piece 61b relative to the electromagnetic transformer 61a and consequently the rate of decrease in the amount of compression G of the coiled spring 41, as shown in FIG. 6F.

On the other hand, since the motor 43 stops rotation at t6, the rotary pulse generator 66 ceases to generate the pulses P66 at the same time. Therefore, the counter 108 having performed additive counting of the pulses P66 after tA finishes it as shown in FIG. 6N and the counter 107 having performed additive counting of the pulses P66 after t4 also finishes it as shown in FIG. 6O.

However, since the motor 43 starts reverse rotation at t7 in response to the pulse P102 which is provided from the comparator 102 at t7, as described above, the rotary pulse generator 66 again yields the pulses P66 after t7, as shown in FIG. 6H.

On the other hand, the control circuit 94 responds to the pulse P102 from the comparator 102 to yield the pulse P103 at t7, as shown in FIG. 6M. The pulse P103 is provided to the counters 107 and 108.

The counters 107 and 108 both respond to the pulse P103 to start at t7 subtractive counting of the pulses P66 which are again produced after t7, as depicted in FIG. 6O and 6N.

The value of the detected output S61 from the displacement detector 61 decrease from V2 with time after t7, as mentioned previously with reference to FIG. 6F. Where the value of the detected output S61 coincides with the value V1 of the pressure set signal S103 from the pressure setting circuit 103 at a time point before or after t9 (hereinafter identified by t9' after t9), the comparator 101 yields the pulse P101B as a next pulse of the pulse P101, as shown in FIG. 6J, and the pulse P101B is applied to the counter 107.

The counter 107, which has continued the subtractive counting of the pulses P66 after t7, responds to the pulse P101B to stop the counting at t10, after which it supplies the arithmetic circuit 109 with the count output S107 which is the difference between the count value of the pulses P66 from t4 to t6 and the count value of the pulses P66 from t7 to t10.

The indenter pressing sleeve 25 continues to rise after t9 also, but the indenter 32 does not move up after t9 as mentioned above; and so that the pressure receiving portion 32b of the indenter 32 is received by the stepped portion 30 of the indenter pressing sleeve 25 after t11, as in the case of the first embodiment.

As a result of this, the amount of contraction G of the coiled spring 41 returns to the reference value g0 at t11 and remains unchanged thereafter and the indenter 32 ascends after t11 at the same speed as the sleeve 25 moves up.

Since the amount of contraction G of the coiled spring 41 returns to the reference value g0 at t11, the pressure detected output S61 from the displacement detector 61 returns to the reference value V0 at t11, as in the case of the first embodiment.

On the other hand, where the indenter pressing sleeve 25 moves up after t9 as described above and at tB its height H reaches the value hA which is the value at tA, the contact 85 of the switch 89 engages the contact 87 which have been held out of contact with each other from tA. Thus the switch 89 is turned ON at tB and yields the switch signal S89 in the ON state, as shown in FIG. 6I. The switch signal S89 is supplied to the counter 108 of the processor 91.

Upon receiving the switch signal S89 at tB, the counter 108 stops the subtractive counting of the pulses P66 started at t7, and supplies the arithmetic circuit 109 with the count output S107 which is the difference between the count value of the pulses P66 from the tA to t6 and the count value of the pulses P66 from t7 to tB.

Since the arithmetic circuit 109 has been supplied with the count output S107 from the counter 107 after t10, as described above, the circuit 109 performs an operation of correcting the value of the count output S107 with the value of the count output S108 from the counter 108 and provides the operated output S109, as the output S91 of the processor 91, to the display 92.

Further, since the indenter 32 moves up after t11, the engaging member 71b of the contactor 71 is received by the lower end face 38 of the guide groove 26 of the indenter pressing sleeve 25 after t12 as in the case of the first embodiment, and as a result of this, after t12 the contactor 71 rises from the position where the contact edge 72 is held in contact with the specimen surface 1a, at the same speed as that of the upward movement of the indenter 32.

When the indenter pressing sleeve 25 moves up together with the indenter 32 after t11 and its end plate portion 28 abuts against the flange 17b of the driving shaft 17 at t14, the stop switch 48 is activated, yielding the stop signal S48 as shown in FIG. 6L. The stop signal S48 is provided to the control circuit 94.

Upon receiving the stop signal S48, the control circuit 94 controls the motor drive circuit 93 to stop the motor 43 at t14 as shown in FIG. 6B, returning the indenter pressing sleeve 25 to initial position where its end plate portion 28 abuts against the flange 17b of the driving shaft 17. This completes a series of operations of the fifth embodiment illustrated in FIGS. 4A to 4C and 5.

As will be understood from the above, according to the fifth embodiment of the present invention, the value of the count output S107 from the counter 107 corresponds to the difference, (m2−m1), between the amount of penetration m1 of the indenter 32 into the specimen 1 when the pressure on the latter assumes the value V1 for impressing the former into the latter to make therein the indentation 51 and the amount of penetration m2 of the indenter 32 into the specimen 1 when the pressure on the latter assumes the value V2 in the upward movement of the former after making the indentation 51.

The difference (m2−m1) represents the hardness or tensile strength of the specimen 1 as in the case of the first embodiment.

The output S108 from the counter 108 corresponds to an error (hereinafter identified by E) in the above-said difference (m2−m1) which is caused in the case where the specimen surface 1a is lowered by the pressure of the indenter 32 during its impression into the specimen 1 but thereafter does not return to the initial height.

Figure 6:
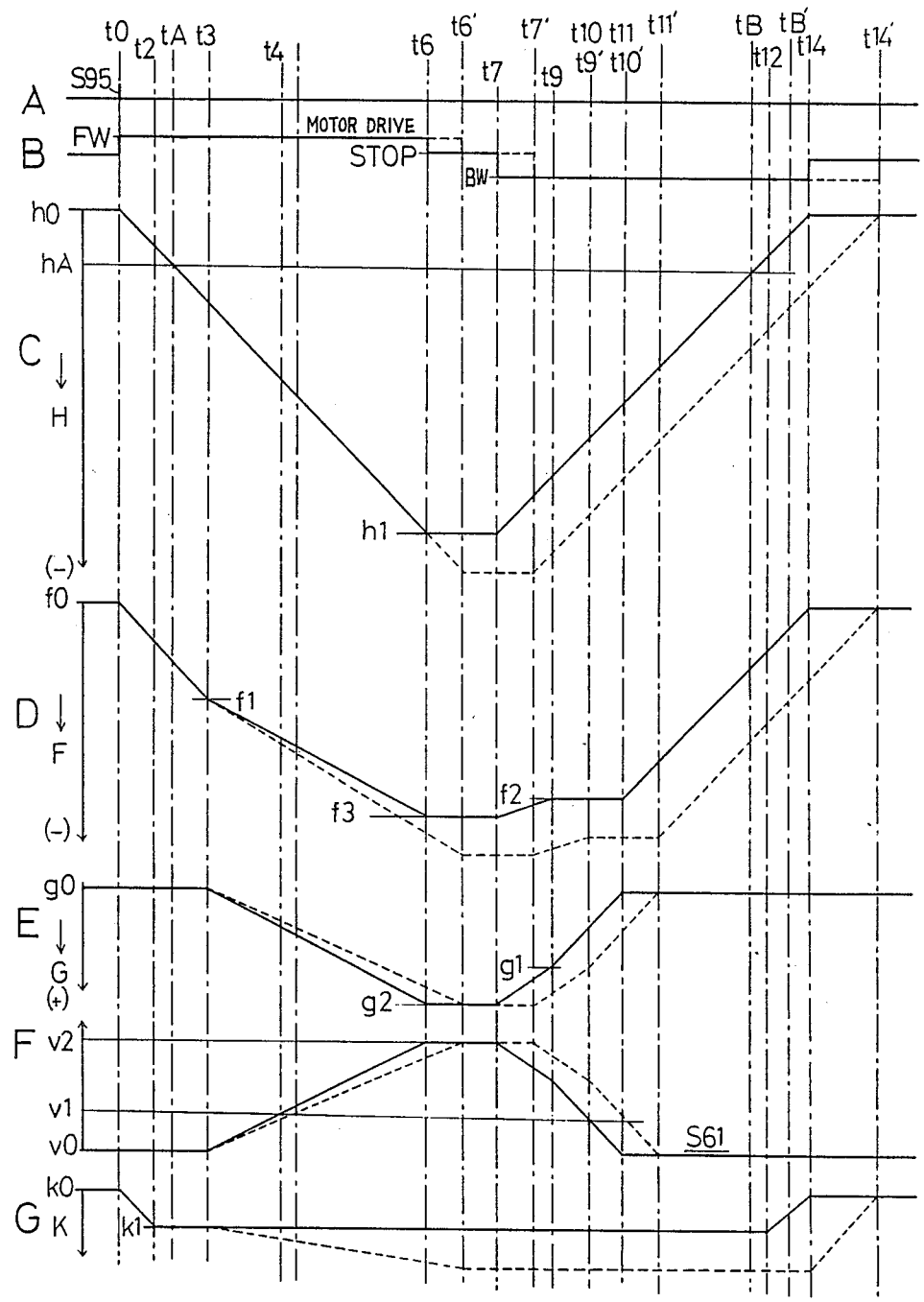
FIGS. 6A to 6W are diagrams explanatory of the operation of the fifth embodiment.

In the above the fifth embodiment of the present invention has been described to perform a series of operations as indicated by the solid lines in FIG. 6 on the assumption that the specimen 1 is one that its surface 1a is not substantially lowered by the pressure of the indenter 32 applied thereto. But in the case where the specimen 1 is one that its surface 1a is lowered by the pressure of the indenter 32 but does not rise to the initial height afterwards, the operations of the fifth embodiment are performed as indicated by the broken lines in FIGS. 6A to 6O and by the full lines in FIGS. 6P to 6W, in which respective time points are identified by the same reference numerals as those in FIGS. 6A to 6O but with primes.

As will be appreciated from the above, the operated output S109 of the arithmetic circuit 109 and accordingly the processed output S91 of the processor 91 has a value of the above-mentioned difference (m2−m1) corrected by the error E.

Accordingly, it is possible, with the fifth embodiment, to measure the hardness and tensile strength of the specimen 1, without the abovenoted error, through utilization of the amounts of penetration m1 and m2.

Embodiment 6

A sixth embodiment of the present invention, though not shown nor described in detail, is identical in construction with the fifth embodiment except the following point.

According to the fifth embodiment described above, in the processor 91 depicted in FIG. 5, the count output S107 of the counter 107 is obtained by additive counting of the pulses P66 from the time t4 of generation of the pulse P101A to t6 and then by subtractive counting of the pulses P66 from t7 to t10, through use of the pulses P101A and P101B which are yielded as shown in FIG. 6J when the indenter pressing force detected output S61 from the displacement detector 61 takes the value V1 at both t4 and t10 as shown in FIG. 6F and the pulse P103 which is yielded from the control circuit 94 in response to the pulse P102 which is generated as shown in FIG. 6K when the detected output S61 takes the value V2 at t6. In the sixth embodiment, however, an operated output corresponding to the count output S107 (which output will hereinafter be referred to as an operated output S200) is obtained by detecting the difference between a count output (hereinafter identified as S201) which is produced by counting the pulses P66 from t3 to t6 and a count output (hereinafter identified as S202) which is produced by counting the pulses P66 from t4 to t6, through use of a pulse (hereinafter identified as P101S) which is generated through use of the output S61 at t3 and the above-mentioned pulses P101A and P102. Since the arrangement therefor is obvious to those skilled in the art, no further description will be given.

According to the sixth embodiment of the present invention, the above-said count output S201 corresponds to the amount of penetration m1 of the indenter 32 into the specimen 1 when the pressure for impressing the former into the latter to make therein the indentation 51 to the depth takes the value V2, and the count output S202 corresponds to the amount of penetration m3 referred to previously in connection with the fifth embodiment.

Therefore, the above-mentioned operated output S200 corresponds to the difference (m3−m1) between the amounts of penetration m3 and m1. The difference (m3−m1) represents the yield stress of the specimen 1, though not described in detail.

Accordingly, the sixth embodiment of the present invention permits measurement of the yield stress of the specimen 1 through utilization of the amounts of penetration m1 and m3.

Embodiment 7

A seventh embodiment of the present invention, though not shown nor described in detail, is identical in construction with the fifth embodiment described previously with respect to FIGS. 4A to 4C and 5, except the following point.

According to this embodiment, a count output (hereinafter identified as S300) corresponding to that S107 in the fifth embodiment is obtained by performing additive counting of the pulses P66 from t3 when the pulse P101S is yields to t6 when the pulse P102 is yielded and then subtractive counting of the pulses S66 from t7 when the pulse P103 is produced to t10 when the pulse P101B is produced, through use of the pulse P101S which is produced at t3 when the indenter 32 moves into contact with the specimen 1 and the afore-mentioned pulses P102, P103 and P101B. Since the arrangement therefor is obvious to those skilled in the art, no further description will be given.

The above-said count output S300 corresponds to the difference (m3−m2) between the amount of penetration m3 of the indenter 32 into the specimen 1 when the pressure for impressing the former into the latter to make therein the indentation 51 to the depth takes the value V2 and the amount of penetration m2 referred to previously in connection with the fifth embodiment. The difference (m3−m2) represents the Young's modulus of the specimen 1, though not described in detail.

Accordingly, the seventh embodiment of the present invention permits measurement of the Young's modulus of the specimen 1 through utilization of the above-mentioned amounts of penetration m2 and m3.

Embodiment 8

An eighth embodiment of the present invention, though not described in detail, is also identical in construction with the fifth embodiment except the following point.

According to this embodiment, a count output (hereinafter identified as S400) corresponding to the count output S107 in the fifth embodiment is obtained by counting the pulses P66 from t3 when the pulse S101S is yields to t6 when the pulse P102 is yielded, through use of the pulse P101S and the above-mentioned pulse P102. Since the arrangement therefor is obvious to those skilled in the art, no further description will be given.

The above-mentioned count output S400 corresponds to the amount of penetration m3 of the indenter 32 into the specimen 1 when the pressure for impressing the former into the latter to make therein the indentation 51 to the depth takes the value V2. The amount of penetration m3 represents the creep strength of the specimen 1.

Accordingly, the eighth embodiment of the present invention makes it possible to measure the creep strength of the specimen 1 through utilization of the amount of penetration m3.

Embodiment 9

Figure 7A:
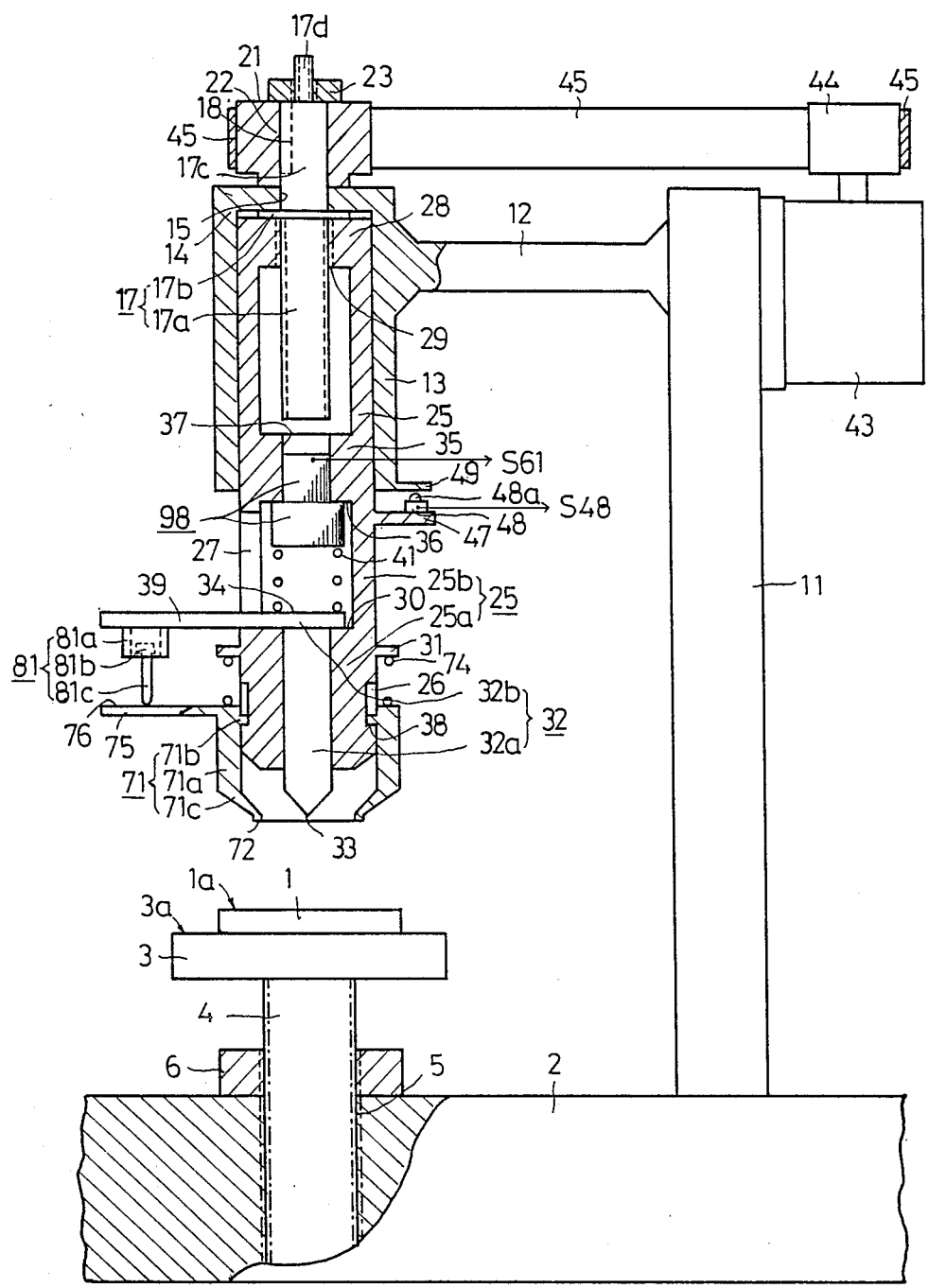
FIG. 7A to 7C are schematic diagrams, partly in section, illustrating the mechanical system of a ninth embodiment of the material testing machine of the present invention.
Figure 7B:
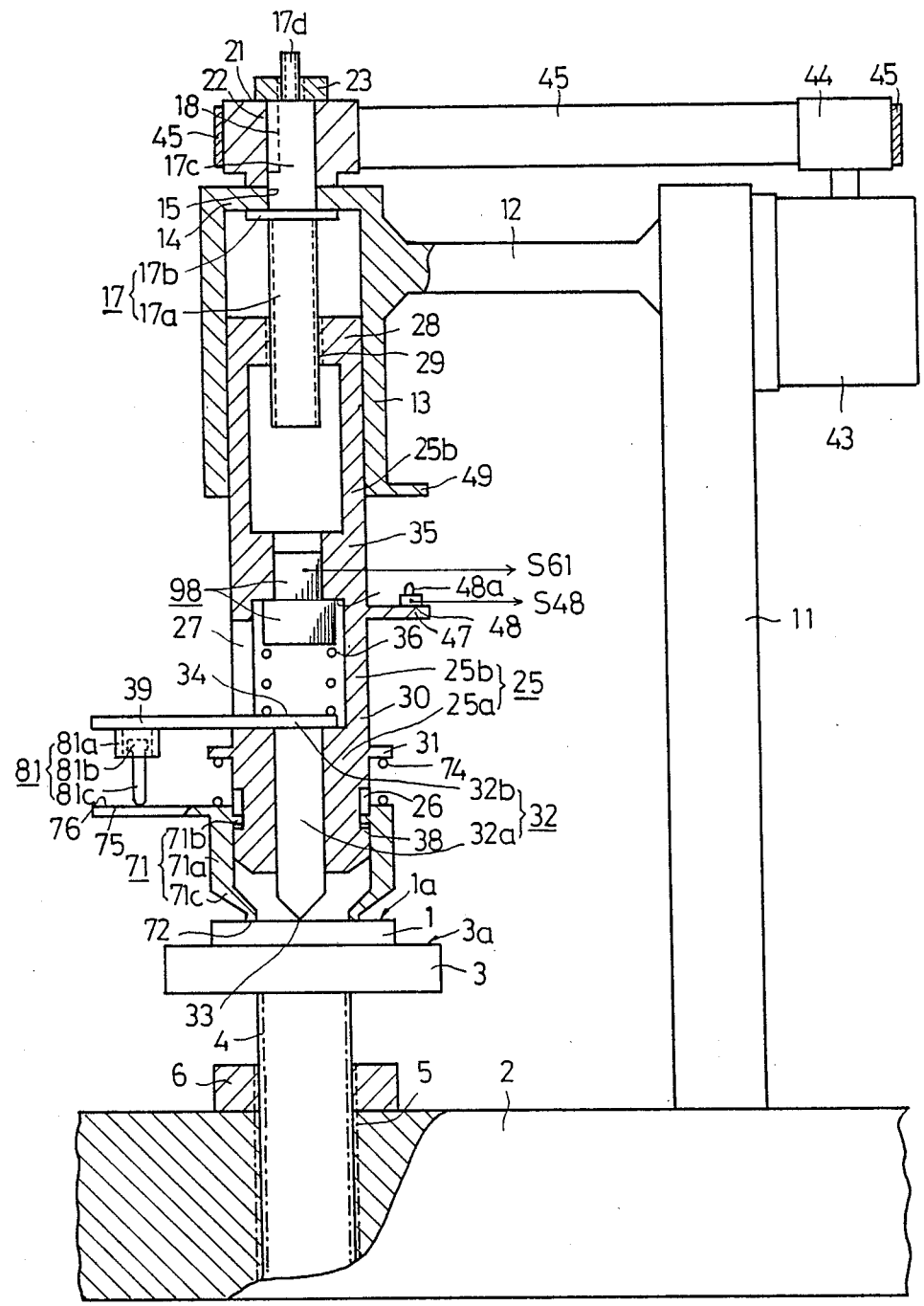
Figure 7C:
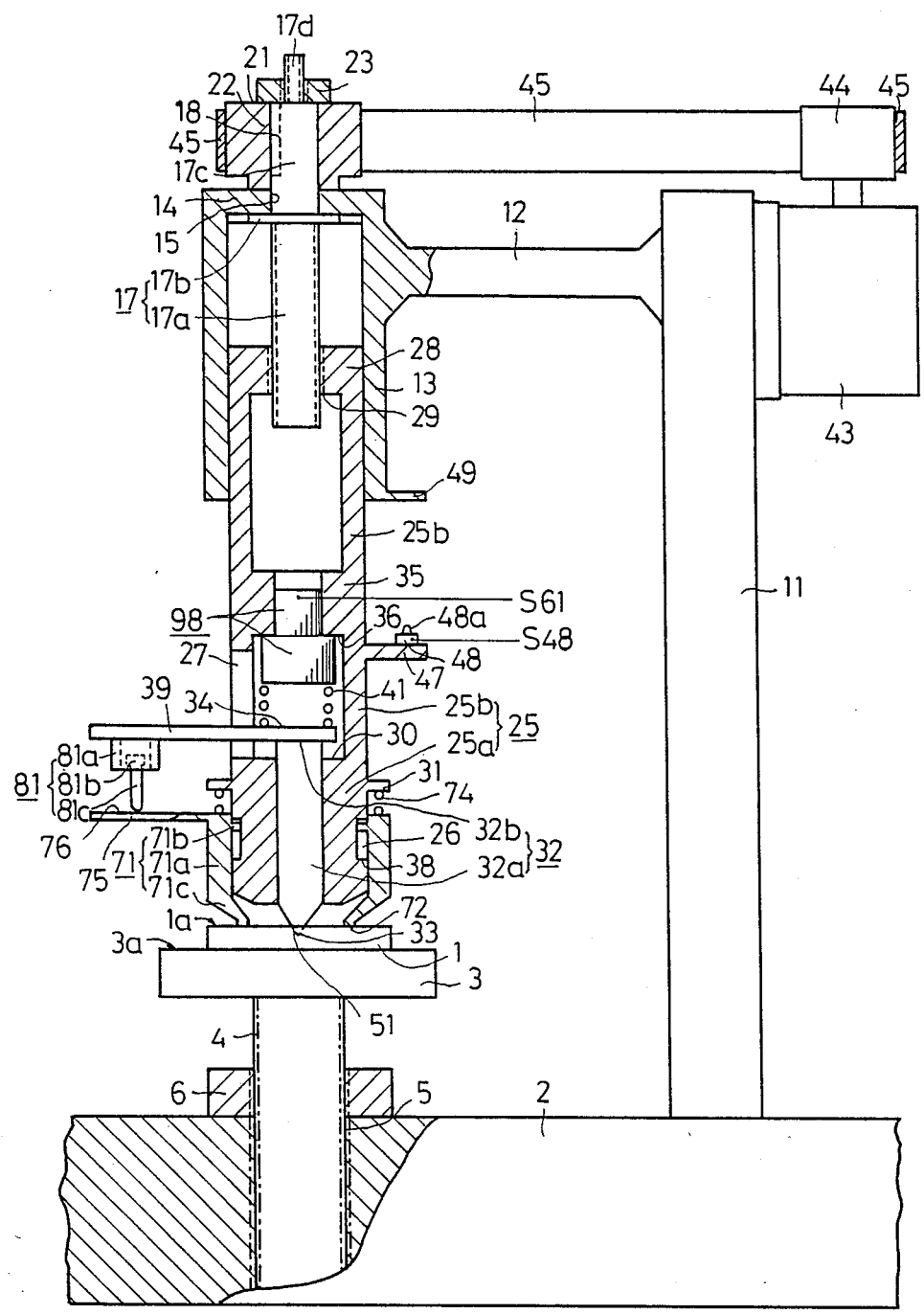

Turning next to FIGS. 7A to 7C, a ninth embodiment of the present invention will be described. This embodiment is identical in construction with the first embodiment except the following point.

The displacement detector 61 for detecting the indenter pressing force in the first embodiment is substituted with a strain gage type indenter pressing force detector 98 which has its upper portion fitted into the hole 37 of the pressing portion 35 of the indenter pressing sleeve 25, with its lower portion fixed to the pressure receiving face 36 of the pressing portion 35, as shown in FIGS. 7A to 7C.

Further, the coiled spring 41 installed between the pressing face 36 of the pressing portion 35 of the indenter pressing portion 25 and the pressure receiving face 34 of the indenter 32 in the first embodiment is disposed between the underside of the indenter pressing force detector 98 and the pressure receiving face 34 of the indenter 32 in this embodiment.

With such an arrangement as described above, when the indenter pressing sleeve 25 further goes down after having brought the pointed end 33 of the indenter 32 into contact with the specimen surface 1a, the coiled spring 41 is compressed and force corresponding to its amount of compression is imparted to the indenter 32 and, as an output representing the amount of compression of the coiled spring 41, to the indenter pressing force detector 98. Accordingly, the indenter pressing force detector 98 yields the detected output S61 which represents the pressure on the specimen 1 applied from the indenter 32, as is the case with the displacement detector 61 described previously with respect to FIGS. 1A to 1C.

Thus, the ninth embodiment of the present invention illustrated in FIGS. 7A to 7C performs similar operations and produces similar effects to those in the case of the first embodiment, though not described in detail.

Embodiment 10, 11 and 12

Tenth, eleventh and twelfth embodiments of the present invention, though not described in detail, are identical in construction with the ninth embodiment except the points described previously with reference to the second, third and fourth embodiments. The tenth, eleventh and twelfth embodiments respectively produce the same operational effects as obtainable with the second, third and fourth embodiments.

Embodiment 13

Figure 8A:
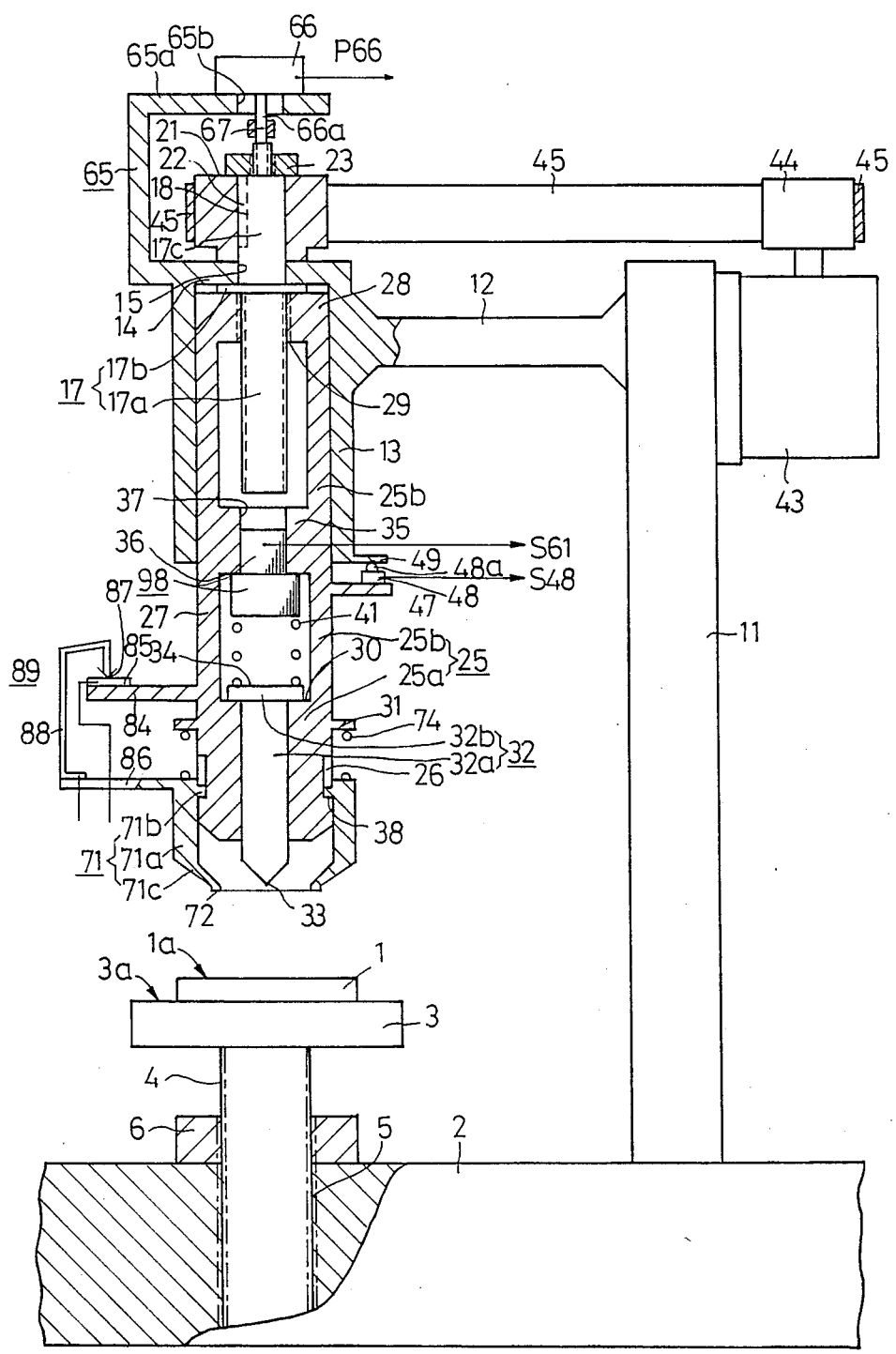
FIGS. 8A to 8C are schematic diagrams, partly in section, illustrating the mechanical system of a thirteenth embodiment of the material testing machine of the present invention.
Figure 8B:
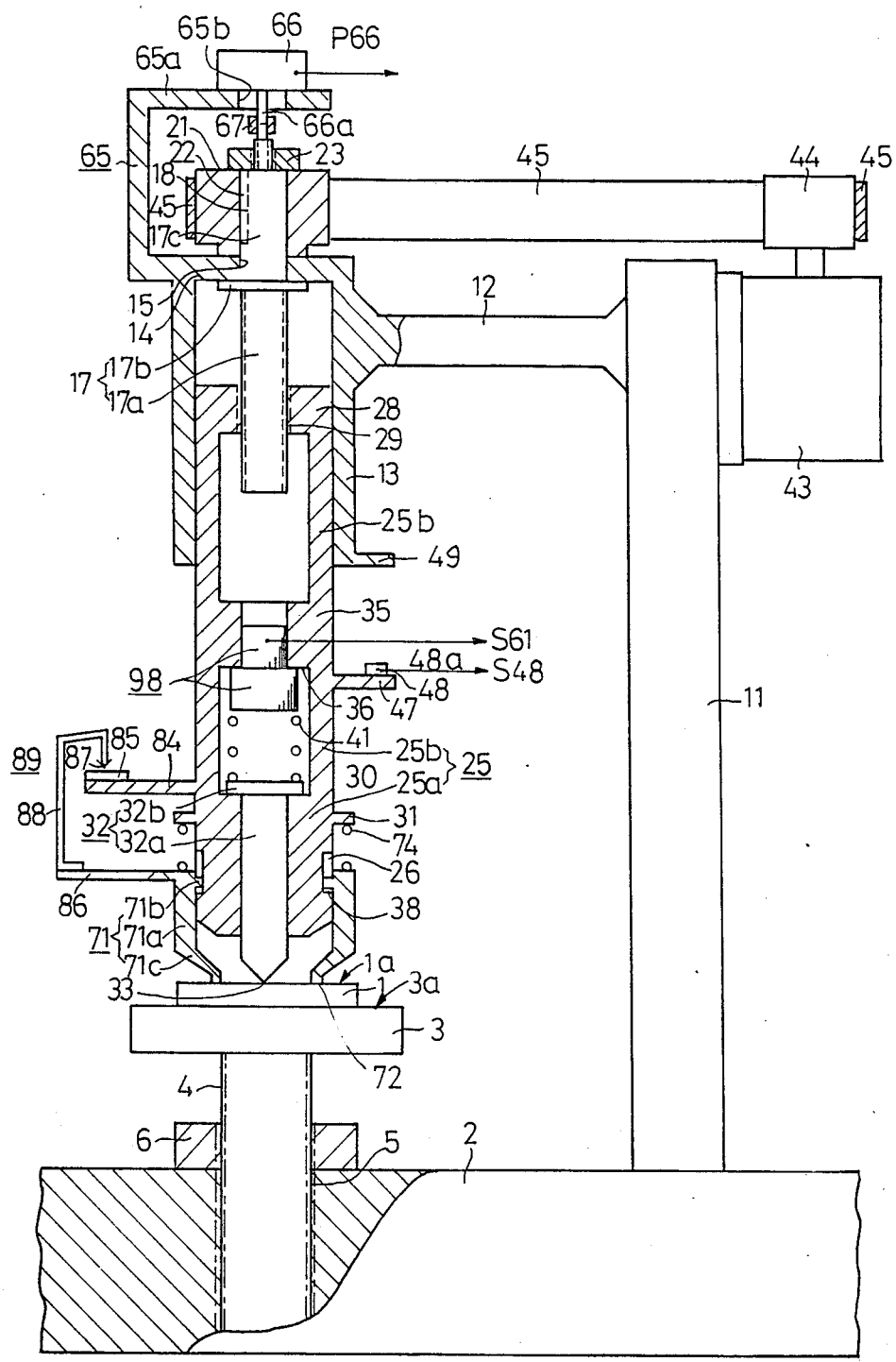
Figure 8C:
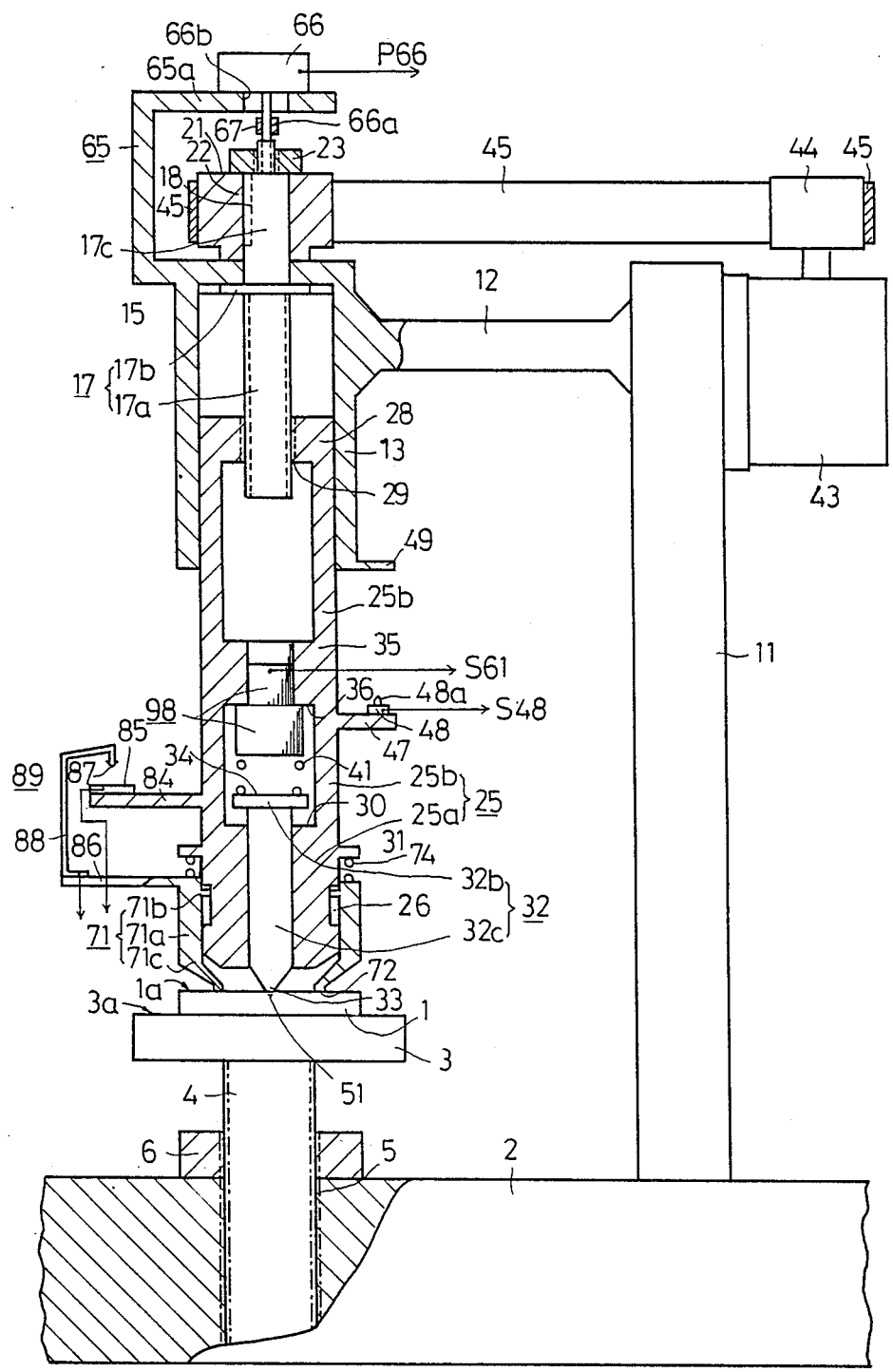

Referring next to FIGS. 8A to 8C, a thirteenth embodiment of the present invention will be described. This embodiment is identical in construction with the fifth embodiment described previously in respect of FIGS. 4A to 4C and 5, except the following point.

The displacement detector 61 for detecting the indenter pressing force in the fifth embodiment is substituted with a strain gage type indenter pressing force detector 98 which has its upper portion fitted into the hole 37 of the pressing portion 35 of the indenter pressing sleeve 25, with its lower portion fixed to the pressure receiving face 36 of the pressing portion 35, as shown in FIGS. 8A to 8C.

Further, the coiled spring 41, which is installed between the pressing face 36 of the pressing portion 35 of the indenter pressing portion 25 and the pressure receiving face 34 of the indenter 32 in the fifth embodiment, is disposed between the underside of the indenter pressing force detector 98 and the pressure receiving face 34 of the indenter 32 in this embodiment.

With such an arrangement as described above, when the indenter pressing sleeve 25 further goes down after having brought the pointed end 33 of the indenter 32 into contact with the specimen surface 1a, the coiled spring 41 is compressed and force corresponding to its amount of compression is imparted to the indenter 32 and, as an output representing the amount of compression of the coiled spring 41, to the indenter pressing force detector 98. Accordingly, the indenter pressing force detector 98 yields the detected output S61 which represents the pressure on the specimen 1 applied from the indenter 32, as is the case with the displacement detector 61 described previously with respect to FIGS. 4A to 4C.

Thus, the thirteenth embodiment of the present invention illustrated in FIGS. 8A to 8C performs similar operations and produces similar effects to those in the case of the fifth embodiment, though not described in detail.

Embodiments 14, 15 and 16

Fourteenth, fifteenth and sixteenth embodiments of the present invention, though not described in detail, are identical in construction with the thirteenth embodiment except the points described previously with reference to the sixth, seventh and eighth embodiments. The fourteenth, fifteenth and sixteenth embodiments respectively produce the same operational effects as these obtainable with the sixth, seventh and eighth embodiments.

As will be appreciated from the above, the foregoing embodiments are merely illustrative of the present invention and should not be construed as limiting of the invention. For example, in FIGS. 1A to 1C and 7A to 7C, the displacement detector 81 for detecting the amount of penetration of the indenter 32 into the specimen 1 may also be arrange so that the electromagnetic transformer 81a serving as a stator is fixed to the contacting member 71 and the engaging member 81c serving as a movable element is held in contact with the indenter 32 accordingly. Similarly, in FIGS. 1A to 1C and 4A to 4C, the displacement detector 61 may also be arranged so that the electromagnetic transformer 61a is fixed to the indenter 32 and the engaging member 61c is held in contact with the indenter pressing sleeve 25 accordingly. Further, contactor 71 may be arranged so that the contact edge 72 makes contact with the specimen table surface 3a. Also, in FIGS. 4A to 4C and 8A to 8C, the contact 85 of the switch 89 may be mounted on the indenter 32. The contacts 85 and 86 may also be mounted on the contacting member 71 and the indenter pressing sleeve 25 or the indenter 32.

It will be apparent that many modifications and variations may be effected without departing from the scope of the novel concepts of the present invention.

What is claimed is:

1. A material testing machine comprising:
   a specimen table for holding a specimen;
   an indenter for impression into the specimen to make therein an indentation;
   an indenter pressing member for pressing the indenter into the specimen;
   indenter pressing force detecting means for detecting the pressure on the specimen applied by the indenter;
   amount of penetration detecting means for detecting the amount of penetration of the indenter into the specimen; and
   an indenter pressing force transmitting member disposed between the indenter pressing member and the indenter;
   wherein the indenter pressing force transmitting member is made of an elastic material; and
   wherein the indenter pressing force detecting means comprises: (a) an indenter pressing force detecting displacement detector provided with a stator fixed to either one of the indenter and the indenter pressing member and a movable element having its free end held in contact with the other one of them; (b) pulse generating means which generates a pulse when the output of the indenter pressing force detecting displacement detector has reached a predetermined value during the movement of the indenter pressing member; and
   wherein the amount of penetration detecting means comprises: (a) a contacting member for contact with the surface of the specimen; (b) an amount of penetration detecting displacement detector provided with a stator fixed to either one of the indenter and the contactor and a movable element having its free end held in contact with the other one of them; and (c) means for latching the output of the amount of penetration detecting displacement detector, as a detected output, by the pulse from the pulse generating means.

2. A material testing machine comprising:
   a specimen table for holding a specimen;
   an indenter for impression into the specimen to make therein an indentation;
   an indenter pressing member for pressing the indenter into the specimen;
   indenter pressing force detecting means for detecting the pressure on the specimen applied by the indenter;
   amount of penetration detecting means for detecting the amount of penetration of the indenter into the specimen; and
   an indenter pressing force transmitting member disposed between the indenter pressing member and the indenter;
   wherein the indenter pressing force transmitting member is made of an elastic material;
   wherein the indenter pressing force detecting means comprises: (a) an indenter pressing force detecting displacement detector provided with a stator fixed to either one of the indenter and the indenter pressing member and a movable element having its free end held in contact with the other one of them; (b) pulse generating means which generates a pulse when the output of the indenter pressing force detecting displacement detector has reached a predetermined value during the movement of the indenter pressing member; and wherein the amount of penetration detecting means comprises: (a) a pulse generator for generating a train of pulses in response to the movement of the indenter pressing member; and (b) counting means for counting the train of pulses from the pulse generator, the counting means being controlled by the pulse from the pulse generating means to count the train of pulses.

3. A material testing machine comprising:
a specimen table for holding a specimen;
an indenter for impression into the specimen to make therein an indentation;
an indenter pressing member for pressing the indenter into the specimen;
indenter pressing force detecting means for detecting the pressure on the specimen applied by the indenter;
amount of penetration detecting means for detecting the amount of penetration of the indenter into the specimen; and
an indenter pressing force transmitting member disposed between the indenter pressing member and the indenter;
wherein the indenter pressing force transmitting member is made of an elastic material;
wherein the indenter pressing force detecting means comprises: (a) an indenter pressing force detecting displacement detector provided with a stator fixed to either one of the indenter and the indenter pressing member and a movable element having its free end held in contact with the other one of them; (b) pulse generating means which generates a pulse when the output of the indenter pressing force detecting displacement detector has reached a predetermined value during the movement of the indenter pressing member; and
wherein the amount of penetration detecting means comprises: (a) a pulse generator for generating a train of pulses in response to the movement of the indenter pressing member; (b) first counting means for counting the train of pulses from the pulse generator, the first counting means being controlled by the pulse from the pulse generating means to count the train of pulses; (c) a contactor which has its free end held in contact with either one of the indenter pressing member or the indenter and the surface of the specimen; (d) a switch which has first and second contacts provided on other one of the indenter pressing member or the indenter and the specimen surface and the contactor, respectively; (e) second counting means for counting the train of pulses from the pulse generator, the second counting means being controlled by a switch signal of the switch; and (f) means for correcting the output of the first counting means by the output of the second counting means and outputting the corrected output.

4. A material testing machine comprising:
a specimen table for holding a specimen;
an indenter for impression into the specimen to make therein an indentation;
an indenter pressing member for pressing the indenter into the specimen;
indenter pressing force detecting means for detecting the pressure on the specimen applied by the indenter, the indenter pressing force detecting means comprising a strain gage type indenter pressing force detector fixed to the indenter pressing member, and pulse generating means which generates a pulse when the output of the strain gage type indenter pressing force detector has reached a predetermined value during the movement of the indenter pressing member;
amount of penetration detecting means for detecting the amount of penetration of the indenter into the specimen; and
an indicator pressing force transmitting member disposed between the strain gage type indenter pressing force detector and the indenter;
wherein the indenter pressing force transmitting member is made of an elastic material; and
wherein the amount of penetration detecting means comprises: (a) a contacting member for contact with the surface of the specimen; (b) an amount of penetration detecting displacement detector provided with a stator fixed to either one of the indenter and the contactor and a movable element having its free end held in contact with the other one of them; and (c) means for latching the output of the amount of penetration detecting displacement detector, as a detected output, by the pulse from the pulse generating means.

5. A material testing machine comprising:
a specimen table for holding a specimen;
an indenter for impression into the specimen to make therein an indentation;
an indenter pressing member for pressing the indenter into the specimen;
indenter pressing force detecting means for detecting the pressure on the specimen applied by the indenter, the indenter pressing force detecting means comprising a strain gage type indenter pressing force detector fixed to the indenter pressing member, and pulse generating means which generates a pulse when the output of the strain gage indenter pressing force detector has reached a predetermined value during the movement of the indenter pressing member;
amount of penetration detecting means for detecting the amount of penetration of the indenter into the specimen; and
an indenter pressing force transmitting member disposed between the strain gage type indenter pressing force detector and the indenter;
wherein the indenter pressing force transmitting member is made of an elastic material; and
wherein the amount of penetration detecting means comprises: (a) a pulse generator for generating a train of pulses in response to the movement of the indenter pressing member; and (b) counting means for counting the train of pulses from the pulse generator, the counting means being controlled by the pulse from the pulse generating means to count the train of pulses.

6. A material testing machine comprising:
a specimen table for holding a specimen;
an indenter for impression into the specimen to make therein an indentation;
an indenter pressing member for pressing the indenter into the specimen;
indenter pressing force detecting means for detecting the pressure on the specimen applied by the indenter, the indenter pressing force detecting means comprising a strain gage type indenter pressing force detector fixed to the indenter pressing member, and pulse generating means which generates a pulse when the output of the strain gage indenter pressing force detector has reached a predetermined value during the movement of the indenter pressing member;

amount of penetration detecting means for detecting the amount of penetration of the indenter into the specimen; and an indenter pressing force transmitting member disposed between the strain gage type indenter pressing force detector and the indenter;

wherein the indenter pressing force transmitting member is made of an elastic material; and wherein the amount of penetration detecting means comprises: (a) a pulse generator for generating a train of pulses in response to the movement of the indenter pressing member; and (b) first counting means for counting the train of pulses from the pulse generator, the first counting means being controlled by the pulse from the pulse generating means to count the train of pulses; (c) a contactor which has its free end held in contact with either one of the indenter pressing member or the indenter and the surface of the specimen; (d) a switch which has first and second contacts provided on other one of the indenter pressing member or the indenter and the specimen surface and the contactor, respectively; (e) second counting means for counting the train of pulses from the pulse generator, the second counting means being controlled by a switch signal of the switch; and (f) means for correcting the output of the first counting means by the output of the second counting means and outputting the corrected output.

* * * * *